(12) United States Patent
Fujii et al.

(10) Patent No.: US 10,071,133 B2
(45) Date of Patent: Sep. 11, 2018

(54) METHOD FOR DESTROYING EXOSOMES, KIT FOR DESTROYING EXOSOMES, AND METHOD FOR ISOLATING EXOSOMES DERIVED FROM NORMAL CELLS

(71) Applicant: MITSUI CHEMICALS, INC., Minato-ku, Tokyo (JP)

(72) Inventors: Ryota Fujii, Chiba (JP); Miwa Ikeda, Mobara (JP); Kazuya Matsumoto, Mobara (JP)

(73) Assignee: MITSUI CHEMICALS, INC., Minato-Ku, Tokyo (JP)

( * ) Notice: Subject to any disclaimer, the term of this patent is extended or adjusted under 35 U.S.C. 154(b) by 0 days.

(21) Appl. No.: 15/557,494

(22) PCT Filed: Mar. 11, 2016

(86) PCT No.: PCT/JP2016/057862
§ 371 (c)(1),
(2) Date: Sep. 12, 2017

(87) PCT Pub. No.: WO2016/143904
PCT Pub. Date: Sep. 15, 2016

(65) Prior Publication Data
US 2018/0055906 A1 Mar. 1, 2018

(30) Foreign Application Priority Data
Mar. 12, 2015 (JP) .................. 2015-049136

(51) Int. Cl.
*A61K 38/16* (2006.01)
(52) U.S. Cl.
CPC .................. *A61K 38/16* (2013.01)
(58) Field of Classification Search
None
See application file for complete search history.

(56) References Cited

U.S. PATENT DOCUMENTS

| | | |
|---|---|---|
| 7,739,055 B2 | 6/2010 | Stephanopoulos et al. |
| 8,288,172 B2 | 10/2012 | Ichim et al. |
| 9,364,601 B2 | 6/2016 | Ichim et al. |
| 9,448,238 B2 | 9/2016 | Ohta et al. |
| 2007/0197773 A1 | 8/2007 | Stephanopoulos et al. |
| 2007/0254006 A1 | 11/2007 | Loose et al. |
| 2009/0304677 A1 | 12/2009 | Ichim et al. |
| 2010/0184693 A1 | 7/2010 | Stephanopoulos et al. |
| 2013/0015118 A1 | 1/2013 | Ichim et al. |
| 2014/0161810 A1 | 6/2014 | Ichim et al. |
| 2014/0166578 A1 | 6/2014 | Ichim et al. |
| 2015/0010913 A1 | 1/2015 | Ohta et al. |

FOREIGN PATENT DOCUMENTS

| | | |
|---|---|---|
| JP | 2009-526862 A | 7/2009 |
| WO | WO 2007/103572 A2 | 9/2007 |
| WO | WO 2013/099925 A1 | 7/2013 |

OTHER PUBLICATIONS

Kime et al. Scientific Reports 5 : 8028 , 2015.*
Matsuzaki et al. (Biochemica et Biophysica Acta 1327, 1997 119-130).*
Blackburn and Gavilanes, The Journal of Biological Chemistry, vol. 255, No. 22, Issue of Nov. 25. pp. 10959-10965, 1980.*
International Search Report (PCT/ISA/210) dated May 31, 2016, by the Japanese Patent Office as the International Searching Authority for International Application No. PCT/JP2016/057862.
Written Opinion (PCT/ISA/237) dated May 31, 2016, by the Japanese Patent Office as the International Searching Authority for International Application No. PCT/JP2016/057862.
Salido-Guadarrama et al., "MicroRNAs transported by exosomes in body fluids as mediators of intercellular communication in cancer", Onco Targets Ther., Jul. 2014, pp. 1327-1338, vol. 7.
Valadi et al., "Exosome-mediated transfer of mRNAs and microRNAs is a novel mechanism of genetic exchange between cells", Nat Cell Biol., Jun. 2007, pp. 654-659, vol. 9.
Lv et al., "Isolation and Quantification of MicroRNAs from Urinary Exosomes/Microvesicles for Biomarker Discovery", Int. J. Biol. Sci., 2013, pp. 1021-1331, vol. 9.
Kosaka et al., "The Roles of Exosome in Cancer Malignancy", Cell Technology, pp. 16-22, vol. 32, No. 1.
Ueda et al., "Effects of cancer cell-derived exosomes", Experimental medicine, pp. 410-414, vol. 29, No. 3.
Ueda, et. al., "Dicer-regulated microRNAs 222 and 339 promote resistance of cancer cells to cytotoxic T-lymphocytes by down-regulation of ICAM-1", Proc. Natl, Acad. Sci. USA, Jun. 2009, pp. 10746-10751, vol. 106, No. 26.
Zhang et al., "Exosome and Exosomal MicroRNA: Trafficking, Sorting, and Function", Genomics Proteomics Bioinformatics, 2015, pp. 17-24, vol. 13.
Ochiya, Exosome Analysis Master Lesson, pp. 27-33, 36-47, 68-69, 76-83.
Yoo et al., "A direct extraction method for microRNAs from exosomes captured by immunoaffinity beads", Anal Biochem., Dec. 2012, pp. 96-98, 431(2).
Eldh et al., "Importance of RNA isolation methods for analysis of exosomal RNA: Evaluation of different methods", Mol. Immunol., Apr. 2012, pp. 278-286, 50(4).
An et al., "Exosomes serve as tumour markers for personalized diagnostics owing to their important role in cancer metastasis", Journal of Extracellular Vesicles, 2015, pp. 1-15.
Rupp et al., "Loss of EpCAM expression in breast cancer derived serum exosomes: Role of proteolytic cleavage", Gynecologic Oncology, 2011, pp. 437-446, vol. 122.

(Continued)

*Primary Examiner* — Jeanette M Lieb
(74) *Attorney, Agent, or Firm* — Buchanan, Ingersoll & Rooney PC

(57) ABSTRACT

A method for destroying exosomes of the present invention includes a step of preparing an antimicrobial peptide; and a step of allowing the antimicrobial peptide to coexist with an exosome to destroy the exosome.

7 Claims, No Drawings
Specification includes a Sequence Listing.

(56) References Cited

OTHER PUBLICATIONS

Hoskin et al., "Studies on anticancer activities of antimicrobial peptides", Biochimica et Biophysics Acta, 2008, pp. 357-375, vol. 1778.

Kubo et al., "Structure and affinity of DNA binding peptides", Nucleic Acids Symposium Series, 2000, pp. 49-50, No. 44.

Dickson et al., "Ribonuclease Inhibitor: Structure and Function", Prog Nucleic Acid Res Mol Biol. 2005, pp. 349-74, vol. 80.

Berger et al., "Inhibition of Intractable Nucleases with Ribonucleoside-Vanadyl Complexes: Isolation of Messenger Ribonucleic Acid from Resting Lymphocytes", Biochemistry, 1979, pp. 5143-5149, 18 (23).

Zhu et al., "Novel method for extracting exsomes of hepatocellular carcinoma cells", World J Gastroenterol, 2014, pp. 6651-6657, vol. 20, No. 21.

Smyth et al., "Biodistribution and delivery efficiency of unmodified tumor-derived exosomes", J control Release, Feb. 2015, pp. 145-55, vol. 199.

Hu et al., "Release of Luminal Exosomes Contributes to TLR4-Mediated Epithelial Antimicrobial Defense", PLoS Pathog, 2013, pp. 1-13, vol. 9, No. 4.

Reis et al., "Bone Marrow-Derived Mesenchymal Stem Cells Repaired but Did Not Prevent Gentamicin-Induced Acute Kidney Injury through Paracrine Effects in Rats", PLoS One, 2012, pp. 1-11, vol. 7, No. 9.

Malhotra et al., "Exosomes: Tunable Nano Vehicles for Macromolecular Delivery of Transferrin and Lactoferrin to Specific Intracellular Compartment", J Biomed Nanotechnol, May 2016, pp. 1101-1114, vol. 12, No. 5.

\* cited by examiner

METHOD FOR DESTROYING EXOSOMES, KIT FOR DESTROYING EXOSOMES, AND METHOD FOR ISOLATING EXOSOMES DERIVED FROM NORMAL CELLS

TECHNICAL FIELD

The present invention is related to a method for destroying exosomes, a kit for destroying exosomes, and a method for isolating exosomes derived from normal cells.

BACKGROUND ART

<Summary of Exosome>

An exosome is an extracellular granule secreted by cells. Specifically, the exosome is a vesicle having a diameter of approximately 30 nm to 100 nm that is released from the cell having a vesicle structure formed of a lipid bilayer. It has been known that the exosome is incorporated into another cell different from the cell that has secreted the exosome (hereinafter referred to as a secreting cell) and thereby plays a role in information signaling between the secreting cell and the other cell (Non-Patent Documents 1 and 2).

<Stability of Exosome>

It has been known that a structure of the exosome membrane is generally stable compared to a structure of the cell membrane. For example, the experimental results are described in Non-Patent Document 3 that a substance contained in the exosome is stably maintained even in a case where the exosome is subjected to a freeze-thaw process for 4 times without adding a stabilizer such as saccharide under the condition of temperature of −20° C. On the other hand, it has been known that cells called animal cells generally cannot bear the freeze-thaw process unless the above described stabilizer is used. Accordingly, it is presumed that the exosome membrane has a stable structure compared to that of the animal cells.

In addition, a step of forming the membrane structure is different between the exosome and the cell. Additionally, the structure of the exosome membrane and the structure of the cell membrane are compared and both are different in the surface area of the membrane and the type of a surface protein present on the surface of the membrane. Even considering this circumstance, it is considered that the structure of the exosome membrane is stable compared to the structure of the cell membrane. Because the exosome is not a living cell, the exosome is not the target for a cell-death program by apoptosis that can be applied to general cells.

<Relationship Between Exosome and Disease>

Various reports have been made recently on the correlation between the exosome and various diseases. Particularly, the exosome released from cancer cells is being focused on and various research results have been reported regarding the influence of the exosome on a particular disease, that is, a cancer. For example, it has been reported that in a case where factors inducing angiogenesis which are contained in the exosome released from the cancer cells are incorporated into healthy vascular endothelial cells, neogenesis of blood vessels around tumor tissues is induced by the factors inducing the angiogenesis, which leads to a possibility of progression of cancer metastasis and invasion (Non-Patent Documents 4 to 6).

In addition, regarding the correlation between the exosome and various diseases, it is also becoming clear that information related to a disease is contained in the exosome. For example, it is described in Non-Patent Document 3 that the exosome present in the blood of a cancer patient contains substances that are biomarkers of cancer (proteins such as PSA, HER2 and EGFR, microRNA such as miR-21 and miR-200a, messenger RNA such as Apbb1ip and ASPN, DNA such as KRAS, various metabolites, or the like).

Particularly, a microRNA contained in the exosome as a substance that is a biomarker of cancer is considered promising as an examination index of cancer. A database of microRNA in living organisms has already been made in miRBase (URL: http://www.mirbase.org/). Among these, 2588 species of human microRNAs are known as of 2015. Furthermore, it has been known that expression profiles in the above described human microRNAs are different depending on the type of the organs and are also different between normal cells and cancer cells. Considering this circumstance, it has been extensively examined to develop techniques for diagnosing the site and progress degree of cancer by using a blood test analyzing microRNA contained in the exosome in blood (Non-Patent Document 7).

<Method for Isolating and Collecting (Collection) and Removing Exosome>

A technique focusing on a method for isolating and collecting (collection) and removing exosomes is as follows.

As the method for collecting the exosome from body fluids of human (blood, saliva, urine and the like) and a medium of cell cultures, an ultracentrifugation method described in Non-Patent Document 8 and the like is the most generally used technique as of 2015. For example, in a case of collecting the exosome from a cell culture supernatant or body fluids, it is possible to remove large contaminants such as cell fragments using a filter and the like, and then perform the ultracentrifugation under the conditions at 4° C. and 100,000 G for 70 minutes to collect the desired exosome. In addition, Non-Patent Document 8 describes a method for collecting an exosome by precipitating the exosome in a cell culture supernatant or body fluids using a co-precipitating agent such as PEG (Non-Patent Document 8).

In addition, Patent Document 1 discloses a technique of adsorptive removal of an exosome by using an antibody that specifically binds to the exosome. Specifically, Patent Document 1 describes a method for adsorptive removal of an exosome by using an antibody that specifically binds to four-pass transmembrane proteins such as CD9, CD63 and CD81 which are present on the surface of a vesicle of the exosome.

Patent Document 2 describes a method for using an antibody that specifically adsorbs to exosomes derived from cancer cells in order to adsorb and remove the exosomes derived from cancer cells secreted by cancer cells.

Non-Patent Documents 9 and 10 disclose a method for destroying and removing an exosome itself by chemically treating a cell membrane of the exosome. Specifically, Non-Patent Document 9 describes a method for using a surfactant and Non-Patent Document 10 describes a method for using phenol, guanidine, and a surfactant.

RELATED DOCUMENT

Patent Document

[Patent Document 1] Pamphlet of International Publication No. 2013/099925
[Patent Document 2] Pamphlet of International Publication No. 2007/103572
[Patent Document 3] PCT Japanese Translation Patent Publication No. 2009-526862

Non-Patent Document

[Non-Patent Document 1] Salido-Guadarrama I, et al., Onco Targets Ther. 2014 Jul. 21; 7:1327-38

[Non-Patent Document 2] Valadi H et al., Nat Cell Biol 2007, 9: 654-659

[Non-Patent Document 3] Int. J. Biol. Sci. 2013, 9; 10:1021-31

[Non-Patent Document 4] Cell Technology, Vol. 32, No. 1, pp 16-22

[Non-Patent Document 5] Experimental medicine, Vol. 29, No. 3, pp 410-414

[Non-Patent Document 6] Ueda, et. al., Proc. Natl, Acad. Sci. USA, 106, 10746-10751, 2009

[Non-Patent Document 7] Genomics Proteomics Bioinformatics 13 (2015) 17-24

[Non-Patent Document 8] Exosome Analysis Master Lesson (YODOSHA CO., LTD.)

[Non-Patent Document 9] Anal Biochem., 2012 Dec. 15; 431 (2):96-8

[Non-Patent Document 10] Mol. Immunol., 2012 April; 50(4):278-86

[Non-Patent Document 11] Journal of Extracellular Vesicles 2015, 4:27522

[Non-Patent Document 12] Gynecologic Oncology 2011, 122:437-446

[Non-Patent Document 13] Biochimica et Biophysica Acta, 1778 (2008), 357-375

[Non-Patent Document 14] Nucleic Acids Symposium Series, 2000, 44 49-50

[Non-Patent Document 15] Prog Nucleic Acid Res Mol Biol. 2005; 80:349-74

[Non-Patent Document 16] Biochemistry, 1979, 18 (23), pp 5143-5149

SUMMARY OF THE INVENTION

Technical Problem

In research fields related to the exosome as of 2015, it is required to develop a system capable of efficiently acquiring a biomarker of cancer contained in the exosome and quantitatively detecting the biomarker with high sensitivity and high reproducibility. In addition, in order to realize such a system, it is considered that it is necessary to establish a technique of efficiently destroying exosomes derived from cancer cells with simple operation, a technique of selectively destroying the exosomes derived from cancer cells without destroying exosomes derived from normal cells, and a technique of quantitatively extracting (isolating) a biomarker contained in the exosome. Furthermore, if it is possible to realize the above described system, applying such a system for early detection and treatment of cancer is considered to be possible in the future.

However, none of the various techniques of the related art described in the section of Background Art satisfies a demand level required for realizing the above described system. Specifically, the inventors of the present invention have found that the various techniques of the related art described in the section of Background Art have the following problems.

First, the method described in Non-Patent Documents 9 and 10 in which a cell membrane of the exosome is chemically treated, is a method for destroying both the exosomes derived from cancer cells and the exosomes derived from normal cells.

In addition, regarding the method described in Non-Patent Documents 9 and 10, in a case of assuming that the method will be applied to treatment of diseases such as cancer metastasis in the future, it is highly probable that an organic compound used for the treatment of the cell membrane will nonspecifically act in vivo. Specifically, since a substance called phenol has a strong denaturation of proteins compared to other compounds, in a case of applying the method described in Non-Patent Document 10 to the treatment of diseases such as cancer metastasis, it is considered that an influence affected by phenol on a component different from the exosome present in vivo is required to be eliminated. Accordingly, it is considered that application of the method described in Non-Patent Documents 9 and 10 to the treatment of diseases such as cancer metastasis in the future, is substantially not possible. Considering this circumstance, there has been a tendency recently for construction of a method for destroying and removing the exosome by using a substance that is unlikely to exhibit a nonspecific action in vivo and that is safe for the organisms, is required.

In addition, as the method for extracting a biomarker contained in the exosome, a technique of extracting a biomarker such as microRNA from the exosomes derived from cancer cells which are collected through an antibody immunization method, is known. For example, Non-Patent Document 11 describes a technique for extracting a biomarker such as microRNA from exosomes after collecting the exosomes through the antibody immunization method. However, there is still room for improvement of the above described technique from the viewpoint of selectively extracting a biomarker derived from cancer cells. Specifically, even where an antibody, that can recognize a characteristic protein present in the exosomes derived from cancer cells as an antigen, is used for collecting the exosomes, since a certain amount of the characteristic protein also coexists in the exosomes derived from normal cells, it is considered that sufficient selectivity cannot be obtained with the technique of extracting the above described biomarker from the viewpoint of distinguishably collecting the exosomes derived from cancer cells and the exosomes derived from normal cells. In addition, it is reported in Non-Patent Document 12 that there is also a case where the characteristic protein present in the exosomes derived from cancer cells is decomposed by in vivo protease and lost from the surface of the exosome, which makes it difficult to collect the exosome.

In addition, similarly, the method described in Patent Documents 1 and 2 is also a technique of adsorptive removal of the exosome by using an antibody with high safety for the organisms, but because the amount of exosomes that can be adsorbed to the antibody is limited, there is a disadvantage that adsorptive removal of a specific amount or more of exosomes is not possible. It has been recognized that there is a tendency that this disadvantage becomes more significant particularly in a case of adsorptive removal of the exosomes by using a column or the like filled with antibodies in a high density. This is because an exosome particle is ten times or more larger than the antibody. In the case of adsorptive removal of the exosomes by using a column or the like filled with antibodies in a high density, a binding point between the antibody and the exosome is densely present in a space. In this case, since the exosome particle size is ten times or more larger than the antibody as described above, the above space is occupied by the exosome particles. Accordingly, in the case of adsorptive removal of the exosomes by using a column or the like filled with antibodies in a high density, a binding point of the antibody that is not involved in the binding (adsorbing) of the exosome particles is generated in the space, and as a result, there is a possibility that a disadvantage of which an adsorbing amount of exosome particles decreases is generated (it is also considered that the fact that the surface area of the exosome is smaller than that of a column particle, and as a result, an amount of antigens present on the surface becomes relatively smaller, also affects the above case).

In addition, it is known that states of the antigen present on the surface of the exosomes differ depending on the types of the exosomes, and the results are greatly affected by a titer and specificity of the antibody. Furthermore, from the viewpoint of collecting the exosome with a high level of purity, there is still room for improvement in the technique of collecting the exosome by using the antibody because it is difficult to perform thorough washing.

As described above, from the viewpoint of realizing the above described system, the fact is that the technique of efficiently destroying the exosomes derived from cancer cells with simple operation, the technique of selectively destroying the exosomes derived from cancer cells, and the technique of quantitatively extracting (isolating) the biomarker contained in the exosome, the techniques being based on the premise that safety for the organisms is guaranteed, have not been established yet.

The present invention provides a technique of destroying and removing an exosome which enables guaranteeing of safety for the organisms, simple and efficient destruction of the exosomes derived from cancer cells, and efficient and selective extraction of a biomarker contained in the exosome.

Solution to Problem

The inventors of the present invention have conducted intensive studies in order to solve the problem in the related art described in the section of Technical Problem. As a result, the inventors of the present invention have found that by using a specific polypeptide, it is possible to establish a technique which enables guaranteeing of safety for the organisms, simple and efficient destruction of the exosomes derived from cancer cells, and efficient and selective extraction of a biomarker contained in the exosome, and therefore have completed the present invention.

According to the present invention, there is provided a method for destroying exosomes including a step of preparing an antimicrobial peptide, and a step of allowing the antimicrobial peptide to coexist with an exosome to destroy the exosome.

Furthermore, according to the present invention, there is provided a kit for destroying exosomes derived from cancer cells, including an antimicrobial peptide in which the antimicrobial peptide is a peptide satisfying the following condition (1) or (2):

(1) the peptide has a chain length of 10 or more and less than 50, a net charge of more than 0 and less than 15, and a ratio of hydrophobic residues of 25% or more and less than 65% (excluding a peptide containing 3 or more S—S bonds, and containing any one of a lysine residue or a valine residue in total amino acids constituting the antimicrobial peptide);

(2) the peptide has a chain length of 2 or more and less than 10, a net charge of 0 or less, and a ratio of hydrophobic residues of less than 25%, and satisfies the following condition (2-1) or (2-2):

(2-1) 3 or more histidine residues are contained and none of a tryptophan residue or a valine residue is contained in the total amino acids constituting the antimicrobial peptide;

(2-2) 1 or more arginine residues are contained and none of a phenylalanine residue, a tryptophan residue, or a valine residue is contained in the total amino acids constituting the antimicrobial peptide.

Furthermore, according to the present invention, there is provided a method for isolating exosomes derived from normal cells, including a step of allowing an antimicrobial peptide satisfying the following condition (1) or (2) to coexist with an exosome, in which the exosome is a mixture of an exosome derived from cancer cells and the exosome derived from normal cells:

(1) the peptide has a chain length of 10 or more and less than 50, a net charge of more than 0 and less than 15, and a ratio of hydrophobic residues of 25% or more and less than 65% (excluding a peptide containing 3 or more S—S bonds, and containing any one of a lysine residue or a valine residue in total amino acids constituting the antimicrobial peptide);

(2) the peptide has a chain length of 2 or more and less than 10, a net charge of 0 or less, and a ratio of hydrophobic residues of less than 25%, and satisfies the following condition (2-1) or (2-2):

(2-1) 3 or more histidine residues are contained and none of a tryptophan residue or a valine residue is contained in the total amino acids constituting the antimicrobial peptide;

(2-2) 1 or more arginine residues are contained and none of a phenylalanine residue, a tryptophan residue, or a valine residue is contained in the total amino acids constituting the antimicrobial peptide.

Advantageous Effects of Invention

According to the present invention, it is possible to provide a technique of destroying and removing an exosome which enables guaranteeing of safety for the organisms, simple and efficient destruction of an exosome derived from cancer cells, and efficient and selective extraction of a biomarker contained in the exosome.

Particularly, according to a method for destroying exosomes of the present invention, it is possible to destroy the exosome derived from cancer cells more safely and selectively than the known technique in which chemical treatment is performed, and more simply, efficiently and selectively than the known technique in which an antibody is used.

In addition, according to the present invention, it is possible to selectively destroy the exosome derived from cancer cells from a body fluid sample in which the exosomes derived from normal cells and the exosomes derived from cancer cells are mixed. In the field of the cancer treatment, it is considered that the techniques of the present invention are useful for application for selection of new biomarkers involved in cancer diseases, inspection and diagnosis by efficient detection of existing cancer markers, and dialysis technique.

DESCRIPTION OF EMBODIMENTS (Antimicrobial Peptide)

First, an "antimicrobial peptide" generally means a polypeptide exhibiting bacteriostatic action or bactericidal action against Gram-negative bacteria, Gram-positive bacteria, fungi, some viruses and the like. On the other hand, an antimicrobial peptide in the method for destroying exosomes of the present embodiment (hereinafter referred to as the present destruction method in some cases) refers to those having destructive activity against exosomes. Among these, it is preferable that an antimicrobial peptide usable in the present destruction method can selectively destroy exosomes derived from cancer cells.

Many types of peptides having a unique function as an antimicrobial peptide have been reported to date. However, it has not yet been reported that known antimicrobial peptides have an action of destroying and removing the exosomes. In addition, among the known antimicrobial peptides, there is a peptide called an "anticancer peptide" exhibiting action of destroying cancer cells (Non-Patent Document 13). Among such anticancer peptides, some of them have less influence on normal cells and low level hemolysis. However, it has not yet been clarified whether the anticancer peptides have an action of selectively destroying the exosomes derived from cancer cells.

In addition, in the results of preliminary examination by present inventors, it was confirmed that many of the above described anticancer peptides have inherently no or a low level of destructive ability against the exosomes derived from cancer cells. Specifically, the present inventors have come to realize the following knowledge.

Firstly, there is a case where the anticancer peptides known to have a net charge of less than 0 and a destructive ability against the cancer cells, sometimes have no or a low level of the destructive ability against the exosomes derived from cancer cells.

Secondly, there is a case where the anticancer peptides such as PR-39 known to exhibit anticancer action, sometimes have no or a low level of the destructive ability against the exosomes derived from cancer cells.

Thirdly, there is a case where the anticancer peptides such as Hepcidin TH2-3 or A6K known to have a degradation property against a cellular membrane of the cancer cells, sometimes have no or a low level of the destructive ability against the exosomes derived from cancer cells.

Based on such circumstances, the present inventors have presumed that there is no relativity or similarity between the mechanism of action of the antimicrobial peptide against the cancer cells and the mechanism of action against the exosomes derived from cancer cells, and both mechanisms of action are different from each other.

In addition, the antimicrobial peptide has a positive charge. However, it is known that a substance having a positive charge generally binds to a compound having a negative charge such as a nucleic acid and forms an insoluble substance and precipitates (Non-Patent Document 14).

Accordingly, it is expected that extracting nucleic acid components such as microRNA from the exosome using the antimicrobial peptide, is not easy. However, the present inventors have completed a technique of extracting nucleic acid components such as microRNA from the exosome using the antimicrobial peptide as the result of intensive studies.

First, specific examples of the antimicrobial peptide of the present embodiment include magainin such as magainin 2, defensin such as defensin HNP-1, cecropin such as lactoferricin, nisin, and cecropin B, buforin such as andropin, moricin, seratotoxin, melittin, dermaseptin, bombinin, brevinin, esculetin, and buforin iib, caerin such as MG2B and caerin 1.1, cathelidin such as LL37, mCRAMP, PR-39, CAP-11, CAP-18, RL-37, CRAMP-1/2, rCRAMP, Prophenin, PMAP-23, PMAP-36, PMAP-37, BMAP-27, BMAP-28, BMAP-34, Bac5, Bac7, and cathelicidin-AL, abaesin, apidaecin, indolicidin, brevinin, protegrin, tachyplesin, drosomycin, maximin, dermaseptin, maculatin, TsAP-2, NRC-03, ascaphin-8, polybia-MPI, NK-2, epinecidin-1, pardaxin 4, NRC-07, K6L9, Pep27, 9R, MG2A, histatin-5, macropin, tuftsin, various HHPHG, A3K, A6K, A9K, hepcidin TH2-3, alloferonl, sesquin, gageostatinC, PNC-28, EP3, BEPT II-1, PTP7, $(Gln^{53})$-Connexin 37, C-reactive protein (CRP), dermcidin such as dermcidin-1L, hepcidin-20, olein, gaegurin, citropin, protamine, and the like. Among these, it is preferable to contain one or more peptides selected from the group consisting of magainin 2, LL-37, protamine and nisin, MG2B, mCRAMP, caerin 1.1, maximin 1, maximin 4, dermaseptin, maculatin 3.1, TsAP-2, NRC-03, ascaphin-8, polybia-MPI, NK-2, epinecidin-1, short α-helical peptides (2) (GIIKKIIKKIIKKIIKKI), pardaxin 4, NRC-07, K6L9, magainin I, buforin IIb, Pep27, 9R, MG2A, short α-helical peptides (1) (GIIKKIIKKI), defensin HNP-1, cecropin B, histatin-5, macropin 1, tuftsin, HHPHG, (HHPHG) 2, (HHPHG) 3, and (HHPHG) 4. Magainin 2 derived from a frog, melittin, MG2B, mCRAMP, caerin 1.1, and/or LL-37 derived from human are preferable.

In addition, the sequence of the antimicrobial peptide is described in various databases shown below.

URL: http://aps.unmc.edu/AP/main.php
URL: http://defensins.bii.a-star.edu.sg/
URL: http://crdd.osdd.net/raghava/cancerppd/
URL: http://peptaibol.cryst.bbk.ac.uk/home.shtml
URL: http://www.cybase.org.au/
URL: http://bactibase.pfba-lab-tun.org/main.php
URL: http://phytamp.pfba-lab-tun.org/main.php
URL: http://www.camp.bicnirrh.res.in/
URL: http://yadamp.unisa.it/
URL: http://split4.pmfst.hr/dadp/
URL: http://db-mml.sjtu.edu.cn/THIOBASE/
URL: http://biotechlab.fudan.edu.cn/database/EnzyBase/home.php
URL: http://biotechlab.fudan.edu.cn/database/lamp/
URL: http://milkampdb.org/home.php
URL: http://dbaasp.org/home.xhtml
URL: http://www.baamps.it/

In addition, the antimicrobial peptide of the present embodiment may be extracted from a living organism containing the antimicrobial peptide, may be artificially synthesized in microbe by a genetic recombination technique, and may be artificially and completely synthesized using an organic synthesis technique such as a solid phase synthesis method. In addition, as long as it is within the range where the destructive activity against exosomes is not impaired, some of the amino acid residues constituting the antimicrobial peptides may be substituted with other amino acid residues, some of the amino acid residues constituting the antimicrobial peptide may be deleted, or another amino acid residue may be inserted in the amino acid residues constituting the antimicrobial peptide. Furthermore, in the antimicrobial peptide of the present embodiment, 2 or more peptides may be linked via a spacer. Furthermore, the antimicrobial peptide of the present embodiment may be subjected to post-translational modifications such as C-terminal modification (amidation and the like), N-terminal modification (acetylation and the like), side chain modification, cyclization, and glycosylation modification. Therefore, the amino acids constituting the antimicrobial peptide of the present embodiment are not limited to the 20 essential amino acids constituting the living body, but may be special amino acids described below.

Examples of the N-terminal modification method (side chain $NH_2$ group modification, side chain SH group modification) include acetylation, 5-FAM, BSA, hexanoic acid, PEN, 5-FAM-Ahx, CBZ, HYNIC, stearic acid, Abz, dansyl, KLH, succinylation, dansyl-Ahx, lauric acid, TMR, acryl decanoic acid, lipoic acid, alloc, DTPA, maleimide, benzoyl, various fatty acids, MCA, biotin, FITC, myristoyl, biotin- Ahx, FITC-Ahx, octanoic acid, BOC, Fmoc, OVA, Br—Ac—, formylation, palmitoyl, dabsyl, DHA, nicotine, ATTO488/550/633/647N/655, Rhodamine Green, rhodamineB, TAMRA, Texas Red, Fluorescein and the like.

Examples of the C-terminal modification method (side chain carboxyl group) include amidation, AFC, AMC, MAPS asymmetric 2 branches, MAPS asymmetric 4 branches, MAPS asymmetric 8 branches, BSA, KLH, Bzl, NHEt, cysteamide, NHisopen, NHMe, OSU, ester (OEt), ester (OMe), ester (OtBu), ester (OTBzl), OVA, p-Nitroanilide, tBu and the like.

Examples of the above described special amino acids include 6-aminocaproic acid, aminobutyric acid, citrulline, cysteine (Acm protected), various D-amino acids, dimethyl-lysine, hydroxy-proline, methyl-lysine, norleucine, ornithine, pyroglutamic acid, trimethyl-lysine, β-alanine, ε-acetyl-lysine, 3-nitro-tyrosine, phosphorylated tyrosine, gamma-GLU, cysteine (tBu), penicillamine, penicillamine, N-methylated leucine, homocysteine, N-methylated valine, homoserine, isoleucine, biotin lysine, cysteine (Acm), N-methylated ALA, N-methylated isoleucine, (L) 2-PAL, (L) 4-CL-PHE, (L) 1-NAL, N-methylated phenylalanine, N-methylated threonine, N-methylated serine, N-methylated tyrosine, alpha amino-butyric acid, beta-ASP, (L)-4-Pal, Lys (5-FAM), methionine sulfone, NMe-Asp, Aib, Abu, Mpa, hydroxy proline, acetylated amino acid, mini-PEG1, methionine sulfoxide, NH2-(PEG) 11-CH2COOH, cyclopentylglycine, selenocysteine, azido-lysine, NH2-(PEG) 2-CH2COOH, NH2-(PEG) 6-CH2CH2COOH, NH2-(PEG) 12-CH2CH2COOH, propargylglycine, 1,2,3,4-tetrahydroisoquinoline-3-carboxylic acid, Lys (TMR), Lys (ivdde), NMe-Nle, NMe-Glu, NMe-Nva, Phg, Ser (octanoic-acid), Dab (Dnp), selenomethionine, carboxyamidomethy, beta-homoleucinelated, cysteine, methylated arginine, Arg (Me) 2 asymmetrical, Arg (Me) 2 symmetrical, Lys (Dde) and the like.

In addition, in a case where the antimicrobial peptide of the present embodiment is cyclized, the linkage between the peptides can be carried out by the cyclization or the like by linking a S—S bond between cysteines, the C-terminal (or side chain carboxyl group) and the N-terminal (or side chain $NH_2$ group and side chain SH group). In addition, the antimicrobial peptide of the present embodiment may be linked via the above described spacer.

It is preferable that in the antimicrobial peptide of the present embodiment, a chain length of the total amino acids constituting the peptide (hereinafter also referred to as the chain length), a net charge, a ratio of hydrophobic residues in the amino acid sequence (hereinafter also referred to as the ratio of hydrophobic residues), and the like are controlled. The chain length represents the number of monomers such as amino acids constituting the antimicrobial peptide. The net charge represents a net electric charge that the peptide has. As a technique of calculating the net charge, various methods are known, but the net charge in the present embodiment is basically the neutral net charge (pH 7.4). In addition, the net charge of the antimicrobial peptide to be described later in examples, adopts a value described in the database (URL: http://aps.unmc.edu/AP/main.php) or a value calculated in the same database.

A lower limit value of the chain length of the antimicrobial peptide of the present embodiment is preferably 10 or more, and more preferably 20 or more. On the other hand, an upper limit value of the chain length is preferably less than 50, and more preferably less than 40.

A lower limit value of the net charge of the antimicrobial peptide of the present embodiment is preferably a value larger than 0, and more preferably a value less than 10. On the other hand, an upper limit value of the net charge is preferably a value less than 15, and more preferably a value less than 10.

A lower limit value of the ratio of hydrophobic residues in the amino acid sequence constituting the antimicrobial peptide of the present embodiment is preferably 0% or more, and more preferably 25% or more. On the other hand, an upper limit value of the ratio of hydrophobic residues is preferably 80% or less, and more preferably less than 65%.

Even if each of the chain length, the net charge, the ratio of hydrophobic residues in the amino acid sequence, or the like is within the above numerical range, in a case where a certain number or more of specific amino acid residues are contained, the destructive ability of the antimicrobial peptide of the present embodiment against the exosomes derived from cancer cells decreases. For example, in a case where 6 or more cysteine residues are contained and any one of a lysine residue or a valine residue is contained, the destructive ability against the exosomes derived from cancer cells decreases. In addition, regarding the peptide in which 6 or more alanine residues are contained and a leucine residue is not contained, the peptide in which a phenylalanine residue and a tryptophan residue are not contained, 1 or more of arginine residues are contained and any one of a valine residue and a leucine residue is contained, and the like, there is a possibility that the destructive ability thereof against the exosomes derived from cancer cells decreases. Therefore, the number of S—S bonds present in the antimicrobial peptide of the present embodiment is preferably less than 3.

Accordingly, it is preferable that the antimicrobial peptide of the present embodiment is a peptide satisfying the following condition (1) or (2).

(1) the peptide has a chain length of 10 or more and less than 50, a net charge of more than 0 and less than 15, and a ratio of hydrophobic residues of 25% or more and less than 65% (excluding a peptide containing 3 or more S—S bonds, and containing any one of a lysine residue or a valine residue in total amino acids constituting the antimicrobial peptide);

(2) the peptide has a chain length of 2 or more and less than 10, a net charge of 0 or less, and a ratio of hydrophobic residues of less than 25%, and satisfies the following condition (2-1) or (2-2):

(2-1) 3 or more histidine residues are contained and none of a tryptophan residue or a valine residue is contained in the total amino acids constituting the antimicrobial peptide;

(2-2) 1 or more arginine residues are contained and none of a phenylalanine residue, a tryptophan residue, or a valine residue is contained in the total amino acids constituting the antimicrobial peptide.

In addition, it is more preferable that the antimicrobial peptide of the present embodiment is a peptide satisfying the following condition:

(Condition) the peptide has a chain length of 20 or more and less than 40, a net charge of 1 or more and less than 10, and a ratio of hydrophobic residues of 25% or more and less than 65% (excluding a peptide containing 3 or more S—S bonds, and containing any one of a lysine residue or a valine residue in total amino acids constituting the antimicrobial peptide).

In addition, in a case of classifying the antimicrobial peptide of the present embodiment in terms of a steric structure thereof, specific examples of the classification include an α helix type antimicrobial peptide such as magainin 2, BMAP-27, BMAP-28, cecropin, LL37, CAP-11, CAP-18, olein, gaegurin, citropine and melitin, a β sheet type antimicrobial peptide such as defensin, lactoferricin and tachyplesin, a complex type antimicrobial peptide such as a linkage peptide of the α helix type antimicrobial peptide and the β sheet type antimicrobial peptide, a peptide having many specific amino acid residues (histatin-5), and the like. Among these, it is confirmed that the peptide classified as the α helix type antimicrobial peptide tends to have a high level of the destructive ability against the exosomes derived from cancer cells as described later in the examples.

Furthermore, the antimicrobial peptide of the present embodiment may be used alone, and two or more types may be used in combination.

(Exosome)

The exosome of the present embodiment is a type of extracellular granule secreted by cells of the living organism, and is a small lipid vesicle that is derived from a late endosomal compartment and has a diameter of approximately 30 nm to 100 nm.

In addition, examples of biomaterials containing the exosome include body fluids such as blood (including component separation), bone marrow fluid, lymph fluid, urine, feces, and saliva, cellular debris, and the like. In the present embodiment, it is possible to use an exosome as long as the exosome is extracted by being subjected to pretreatment by a general method depending on the biomaterials.

The exosome of the present embodiment may be an exosome derived from any animal species. Specific examples of the exosome include exosomes derived from warm-blooded animals such as humans, mice, rats, monkeys, dogs, cats, cattle, horses, and birds.

In addition, the exosome of the present embodiment may be an exosome derived from any cell species. Specific examples of the cell species from which the exosome is derived include tumor cells, dendritic cells, reticulocytes, T cells, B cells, platelets, epithelial cells, and the like.

Among these, the exosome of the present embodiment preferably includes exosomes derived from tumor cells involved in metastasis of cancer cells, that is, exosomes derived from cancer cells and secreted by cancer cells. In other words, the exosome of the present embodiment may only include the exosomes derived from cancer cells and secreted by cancer cells, or may be a mixture of the exosomes derived from cancer cells and exosomes derived from normal cells, but it is preferable that the exosome includes the exosomes derived from cancer cells. In addition, in a case where the exosome of the present embodiment is a mixture of the exosomes derived from cancer cells and the exosomes derived from normal cells, the exosomes derived from cancer cells can be destroyed selectively as will be described later in examples.

Specific examples of the cancer cells secreting the exosomes derived from cancer cells of the present embodiment include breast cancer cells, esophageal cancer cells, stomach cancer cells, appendiceal cancer cells, colorectal cancer cells, uterine body cancer cells, cervical cancer cells, ovarian cancer cells, brain tumor cells, liver cancer cells, gallbladder cancer cells, bile duct cancer cells, pancreatic cancer cells, adrenal cancer cells, gastrointestinal stromal tumors, mesothelioma, laryngeal cancer cells, oral cavity cancer cells (cancer of the floor of the oral cavity, gingival cancer, tongue cancer, buccal mucosa cancer, and salivary gland cancer), sinus cancer cells (maxillary sinus cancer, frontal sinus cancer, ethmoid sinus cancer, and sphenoid sinus cancer), thyroid cancer cells, renal cancer cells, lung cancer cells, osteosarcoma, prostate cancer cells, testicular tumor, renal cell cancer cell, bladder cancer cell, rhabdomyosarcoma, skin cancer cell, anal cancer cell, leukemia, lymphoma, Hodgkin's disease, multiple myeloma, and the like.

<Method for Extracting Exosomes>

Various methods for extracting exosomes will be described below.

(Ultracentrifugation Method)

First, a method of extracting an exosome fraction using an ultracentrifuge will be described.

In a case of extracting the exosome fraction directly from cells, a desired exosome fraction can be extracted by using the following method that is a method of performing ultracentrifugation to a cell culture supernatant by a method described later, for example. However, various treatment conditions such as centrifugation are not limited to the conditions described later.

First, the supernatant of culture fluid of the target cell secreting the exosome is centrifuged at 2,000 G at room temperature, which are the conditions in which the exosome fraction does not precipitate, for 15 minutes, and then the insoluble portion is separated. Next, the supernatant fraction obtained is centrifuged at 110,000 G for 70 minutes, and the exosome is precipitated thereby. Thereafter, it is possible to recover a desired exosome fraction by removing the supernatant fraction.

(Gel Filtration Method)

Next, a method of extracting an exosome fraction by gel filtration will be described.

In a case of extracting the exosome fraction from a cell culture supernatant, a desired exosome fraction can be extracted by the following method of performing treatment using a gel filtration method, for example. However, various treatment conditions such as centrifugation are not limited to the conditions described later.

First, the supernatant of culture fluid of the target cell secreting the exosome is subjected to centrifugation at 2,000 G at room temperature, which are the conditions in which the exosome fraction does not precipitate, for 15 minutes, and then the insoluble portion is separated. After removing this insoluble portion, centrifugation is performed at room temperature at 12,000 G which is a rate faster than the first centrifugation, which are the conditions in which the exosome fraction does not precipitate, for 35 minutes, and therefore the supernatant fraction and impurities are separated from each other. Next, the obtained supernatant fraction is provided in a gel filtration column and the eluate obtained thereby is measured for the absorbance at 260 nm, and a fraction with high absorbance is recovered as a desired exosome fraction. The gel filtration column may be a self-built product with a purchased carrier, or may be a commercially available product such as Sephacryl S-400 HR (manufactured by GE Healthcare Bio-Sciences Corp.).

(Extraction from Specimen)

Next, a method of extracting an exosome fraction from a specimen sample such as blood will be described.

In a case of obtaining the exosome fraction from a specimen sample such as blood, after plasma components or serum are isolated according to a known method, the extraction can be performed by a method based on the case of extracting the exosome fraction from the cell culture supernatant. In a case where the exosome fraction is extracted from specimen such as urine, saliva, perspiration, or cerebrospinal fluid, after removing contaminants according to a known method, the extraction can be performed by a method based on the case of the cell culture supernatant.

(Antibody Immunization Method)

Next, a method of extracting an exosome fraction using an antibody will be described.

As an alternative technique to the ultracentrifugation method, an antibody immunization method is known. An antibody available is not particularly limited as long as the antibody can recognize a substance present only on the surface layer of the exosome in the blood as an antigen. Specific examples of the antigen include proteins such as CD9, CD63 and CD81 which belong to a family of four-pass transmembrane proteins called tetraspanins, and proteins specific to the exosomes derived from cancer cells such as epithelial cell adhesion molecule (EpCAM) and human epidermal growth factor receptor type2 (HER2). In addition, examples thereof include CD3, CD4, CD8, CD14, CD15, CD19, CD20, CD41, CD51, CD61, CD62e, CD66b, CD105, CD144, CD235a, Annexin V, Glycoprotein A, Valpha24/Vbeta11, and the like. These antibodies are generally used in a state of being supported by a carrier.

<Method for Destroying Exosomes>

The method for destroying exosomes of the present embodiment include a step of preparing an antimicrobial peptide and a step of destroying an exosome by allowing the antimicrobial peptide to coexist with the exosome. According to such a method, it is possible to efficiently remove the exosome in a sample compared to the conventional method. In addition, this method is carried out ex vivo, and is a technique capable of performing destruction of the exosome under mild conditions on components other than the exosome in a sample. In such a method, it is preferable to perform incubation at a predetermined temperature and time after allowing the antimicrobial peptide to coexist with the exosome. Furthermore, according to this method, it is possible to simplify the working procedure in the destruction process of the exosome.

In the method for destroying exosomes of the present embodiment, regarding the content of the exosome amount and the antimicrobial peptide amount in an incubated solution that is prepared by mixing the antimicrobial peptide and the exosome in a coexisting manner, it is preferable that 100 µM or lower of antimicrobial peptide is contained, it is more preferable that 10 µM or lower of antimicrobial peptide is contained, and it is further more preferable that 1 µM or lower of antimicrobial peptide is contained, with respect to $1 \times 10^8$ particles/mL of the exosome. In that case, the concentration can be adjusted using saline or a buffer such as PBS.

Regarding an incubating temperature of the antimicrobial peptide and the exosome in the method for destroying exosomes of the present embodiment, an optimal value at which the destructive activity is maximized differs depending on the type of antimicrobial peptide, a lower limit value of the incubating temperature is preferably 0° C. or higher, and more preferably 20° C. or higher. On the other hand, an upper limit value of the incubating temperature is preferably 70° C. or lower, and more preferably 40° C. or lower.

A lower limit value of incubating time of the antimicrobial peptide and the exosome in the method for destroying exosomes of the present embodiment is preferably 1 second or more, and more preferably 10 minutes or more. On the other hand, an upper limit value of the incubating time is preferably 72 hours or less, and more preferably 48 hours or less.

In addition, in the method for destroying exosomes of the present embodiment, the incubated solution that is prepared by mixing the antimicrobial peptide and the exosome in a coexisting manner may contain an additive component other than saline or a buffer such as PBS. Specific examples of such additives include reagents such as RNase inhibitor for stabilizing a biomarker and reagents such as protease inhibitor and BSA for stabilizing a peptide. Among these, in a case of extracting a ribonucleic acid biomarker contained in the exosome, it is preferable to contain the RNase inhibitor as an additive.

As the above described RNase inhibitor, RNase inhibitors derived from mammals (derived from human placenta, derived from a mouse, derived from a pig, and the like) are mainly used (Non-Patent Document 15). The RNase inhibitor is a protein of approximately 50 kDa and becomes inactivated by non-covalently binding to ribonucleases B, and C. In addition, it is known that the RNase inhibitor does not act on RNase T1, T2, H, U1, U2, and CL3.

Furthermore, stabilizers based on complexes of oxovanadium (IV) and ribonucleoside may also be used (Non-Patent Document 16).

The above described various additives may be used alone, or two or more may be used in combination.

In the method for destroying exosomes of the present embodiment, regarding an amount of additives added to the incubated solution that is prepared by mixing the antimicrobial peptide and the exosome in a coexisting manner, a general amount in the technical field can be arbitrarily selected within a range in which the destructive activity of the exosome, a target biomarker, or biological safety are not adversely affected. For example, for the RNase inhibitor, the amount is 0.01 U to 20 U/µL, preferably 0.1 U to 1 U/mL.

(Carrier Contact Method)

The antimicrobial peptide of the present embodiment may be immobilized on a carrier. It is known that even if a specific peptide having a bactericidal action called an antimicrobial peptide is immobilized on a carrier or the like so as to be used, the peptide is able to maintain the function thereof (Patent Document 3 and the like).

A carrier used in the method for destroying exosomes of the present embodiment may be a known carrier as long as the carrier is capable of chemically or physically binding the antimicrobial peptide or the above described antibody. Specific examples of the carrier include polyamide, polyethylene glycol, sepharose, polyvinyl alcohol, cellulose, silica, silicon, titanium, iron, and the like. Among these, sepharose and cellulose are preferable, and sepharose is more preferable from the viewpoint of safety in use.

In addition, in a case where a sample containing the exosome is blood containing the exosome, a dialysis membrane for hemodialysis can also be used as a carrier for immobilizing the antimicrobial peptide. Specific examples of the dialysis membrane for hemodialysis include cellulose, cellulose acetate, polysulfone, polyether sulfone, polymethyl methacrylate, ethylene vinyl alcohol copolymer, polyacrylonitrile, polyester polymer alloy, polyallyl ether sulfone, and the like.

In addition, the peptide may be a complex immobilized on an antibody consisting of an amino acid sequence different from the antimicrobial peptide, or the complex may be immobilized on the carrier. The antibody used is preferably an antibody that specifically binds to the exosome. Accordingly, by allowing the exosome to interact with the antibody, it is possible to destroy the exosome with the antimicrobial peptide while the exosome is adsorbed to the antibody.

In a case of using the antimicrobial peptide immobilized on the carrier, or the complex immobilized on the carrier, it is also possible to fill a column with the carrier having the antimicrobial peptide so as to be used. An exosome can be destroyed efficiently by filtering a sample containing the exosome through the column filled with the carrier having the antimicrobial peptide.

In the method for destroying exosomes of the present embodiment, in a case of using the antimicrobial peptide immobilized on the antibody or the carrier, a spacer substance having a predetermined length may be interposed between the antimicrobial peptide and the carrier, between the antibody and the carrier, or between the antimicrobial peptide and the antibody, as long as the purpose of the present invention is not impaired. Specific examples thereof include polyethylene glycol, unsaturated hydrocarbon, peptide and the like.

The spacer substance is a generic term for components capable of linking two substances via a functional group. Specific examples of the functional group include an amino group, a hydroxyl group, a carboxyl group, a thiol group and the like. In addition, a binding mode between the spacer, the antibody, carrier, and antimicrobial peptide is not particularly limited. Examples of a combination of the carrier and the spacer substance include commercially available products such as HiTrap NHS-activated HP Columns (manufactured by GE Healthcare).

Even in the case of the carrier contact method, the above described additives may be added to a solution to be subjected to column extraction.

The effect of the method for destroying exosomes using the antimicrobial peptide of the present embodiment will be explained below.

According to the method for destroying exosomes using the antimicrobial peptide of the present embodiment, safety for the organisms is guaranteed, and it is possible to simply and efficiently destroy the exosomes derived from cancer cells. In addition, according to the present destruction method, it is possible to efficiently destroy the exosomes derived from cancer cells with simple operation compared to the conventional technique.

In addition, the method for destroying exosomes using the antimicrobial peptide of the present embodiment can be favorably used for extracting a biomarker contained in the exosome. Using the above described destruction method of the present embodiment, it is possible to suppress destruction of the exosomes derived from normal cells and to selectively destroy the exosomes derived from cancer cells. Therefore, in the field of the cancer treatment, it is considered that the destruction method of the present embodiment is useful for application for selection of new biomarkers involved in cancer diseases, inspection and diagnosis by efficient detection of existing cancer markers, and dialysis technique.

Regarding a method for extracting a biomarker contained in the exosome, the solution after destruction by the antimicrobial peptide can be extracted by a known method. For example, microRNA can be extracted using a commercially available RNA extraction kit.

For detection of microRNAs, a generally known method in which measurement is performed using a PCR apparatus, especially a real-time PCR apparatus, after obtaining cDNA from the extracted microRNA using reverse transcriptase, can be adopted, for example.

In addition, according to the method for destroying exosomes of the present embodiment, it is possible to destroy and remove the exosome in a sample by using a substance with safety for the organisms. In a case of using this method, it becomes possible to efficiently remove the exosome in a sample compared to the conventional method. In addition, according to the method for destroying exosomes of the present embodiment, for example, it is possible to efficiently destroy and remove the exosome in a sample under conditions in which components other than the exosome in a sample is prevented from being destroyed. Accordingly, in a case of using, for example, a blood sample collected from a living body of a cancer patient as a sample containing the exosome, it is possible to destroy the exosomes derived from cancer cells while preventing the components other than the exosome in a blood sample from being destroyed. Considering these circumstances, the method for destroying exosomes of the present embodiment can be said to be applicable to a suppression system of cancer cell metastasis in the future.

Accordingly, in a case where a sample containing the exosome is blood containing the exosome for example, it becomes possible to use the carrier having the antimicrobial peptide as a constituent of a blood circulation device for destroying the exosome.

<Kit for Destroying Exosomes Derived from Cancer Cells>

A kit for destroying exosomes derived from cancer cells of the present embodiment is used for the above described destruction method and contains the antimicrobial peptide. In addition, the antimicrobial peptide contained in such a destruction kit can selectively destroy the exosomes derived from cancer cells and is a peptide satisfying the following condition (1) or (2):

(1) the peptide has a chain length of 10 or more and less than 50, a net charge of more than 0 and less than 15, and a ratio of hydrophobic residues of 25% or more and less than 65% (excluding a peptide containing 3 or more S—S bonds, and containing any one of a lysine residue or a valine residue in total amino acids constituting the antimicrobial peptide);

(2) the peptide has a chain length of 2 or more and less than 10, a net charge of 0 or less, and a ratio of hydrophobic residues of less than 25%, and satisfies the following condition (2-1) or (2-2):

(2-1) 3 or more histidine residues are contained and none of a tryptophan residue or a valine residue is contained in the total amino acids constituting the antimicrobial peptide.

(2-2) 1 or more arginine residues are contained and none of a phenylalanine residue, a tryptophan residue, or a valine residue is contained in the total amino acids constituting the antimicrobial peptide.

In addition, the kit for destroying exosomes derived from cancer cells of the present embodiment preferably further include the above describe RNase inhibitor from the viewpoint of efficiently destroying the exosomes derived from cancer cells.

<Method of Isolating Exosomes Derived from Normal Cells>

Since the above described destruction method is a technique capable of selectively destroying the exosomes derived from cancer cells, the method can also be used for isolating the exosomes derived from normal cells. Specifically, a method of isolating exosomes derived from normal cells of the present embodiment include a step of allowing the antimicrobial peptide to coexist with the exosome, but the exosomes used in such a method is needed to be a mixture of the exosomes derived from cancer cells and the exosomes derived from normal cells. Furthermore, since the antimicrobial peptide used in the method of isolating exosomes derived from normal cells of the present embodiment is required to selectively destroy the exosomes derived from cancer cells, the peptide is a peptide satisfying the above described condition (1) or (2).

In addition, the method of isolating exosomes derived from normal cells of the present embodiment preferably further include a step of adsorptive removal of a destruction residue of the exosome derived from cancer cells. Accordingly, it is possible to extract the exosomes derived from normal cells with high purity.

Although the embodiments of the present invention have been described, these are examples of the present invention and are not limited thereto, and does not hinder the adoption of various constitutions other than the above.

The present invention includes the following aspects.

1. A method for destroying exosomes, comprising:
a step of preparing an antimicrobial peptide; and
a step of allowing the antimicrobial peptide to coexist with an exosome to destroy the exosome.

2. The method for destroying exosomes according to 1, further comprising a step of preparing a sample containing the exosome before the step of destroying exosomes.

3. The method for destroying exosomes according to 1 or 2, in which the destruction method is carried out ex vivo.

4. The method for destroying exosomes according to any one of 1 to 3, in which the exosome is an exosome derived from cancer cells.

5. The method for destroying exosomes according to any one of 1 to 4, in which the antimicrobial peptide is a polypeptide consisting of 10 or more and 50 or less amino acid residues.

6. The method for destroying exosomes according to any one of 1 to 5, in which the antimicrobial peptide contains 1 or more peptides selected from the group consisting of magainin 2, LL-37, protamine, and nisin.

7. The method for destroying exosomes according to any one of 1 to 6, in which the step of preparing an antimicrobial peptide comprises a step of preparing the antimicrobial peptide immobilized on a carrier.

8. The method for destroying exosomes according to any one of 1 to 6, in which the step of preparing an antimicrobial peptide comprises a step of preparing the antimicrobial peptide immobilized on an antibody.

9. The method for destroying exosomes according to 8, in which the antibody is an antibody that specifically binds to the exosome.

10. The method for destroying exosomes according to 8 or 9, in which the destruction step comprises a step allowing the exosome to interact with the antibody and destroying the exosome interacted with the antibody by the antimicrobial peptide.

11. A kit for destroying exosomes, comprising an antimicrobial peptide.

12. The kit for destroying exosomes according to 11, in which the antimicrobial peptide is a polypeptide consisting of 10 or more and 50 or less amino acid residues.

13. The kit for destroying exosomes according to 11 or 12, in which the antimicrobial peptide contains 1 or more peptides selected from the group consisting of magainin 2, LL-37, protamine, and nisin.

14. The kit for destroying exosomes according to any one of 11 to 13, in which the antimicrobial peptide is immobilized on a carrier.

15. The kit for destroying exosomes according to any one of 11 to 13, in which the antimicrobial peptide is immobilized on an antibody.

16. The kit for destroying exosomes according to 15, in which the antibody is an antibody that specifically binds to the exosome.

17. A method for using an antimicrobial peptide, comprising a step of destroying exosomes by allowing the antimicrobial peptide to coexist with the exosome.

18. The method for using an antimicrobial peptide according to claim 17, in which the exosome is destroyed in the destruction step.

EXAMPLES

Hereinafter, the present invention will be described with reference to examples and comparative examples, but the present invention is not limited thereto.

<Preparation of Antimicrobial Peptide>

Characteristics of the antimicrobial peptide used in each example are shown in Table 1 below.

TABLE 1

| sample No. | Name of antimicrobial peptide | Manufacturer | Sequence number |
|---|---|---|---|
| 1 | Magainin 2 | Bachem | 1 |
| 2 | Nisin | Sigma | 2 |
| 3 | Lactoferricin | Sigma | 3 |
| 4 | LL-37 | Bachem | 4 |
| 5 | Melittin | Bachem | 5 |
| 6 | MG2B | Genscript | 6 |
| 7 | mCRAMP | Eurofins | 7 |
| 8 | Caerin 1.1 | Filgen | 8 |
| 9 | Maximin 1 | Sigma | 9 |
| 10 | Maximin 4 | Eurofins | 10 |
| 11 | Dermaseptin | Bachem | 11 |
| 12 | Maculatin 3.1 | Eurofins | 12 |
| 13 | TsAP02 | Sigma | 13 |
| 14 | NRC-03 | Signam | 14 |
| 15 | Ascaphin-8 | Eurofins | 15 |
| 16 | Polybia-MPI | Filgen | 16 |
| 17 | NK-2 | Sigma | 17 |
| 18 | Epinecidin-1 | Bachem | 18 |
| 19 | Short α-helical peptides (2) | Sigma | 19 |
| 20 | Pardaxin 4 | Eurofins | 20 |
| 21 | NRC-07 | Sigma | 21 |
| 22 | K6L9 | Filgen | 22 |
| 23 | Magainin I | Bachem | 23 |
| 24 | Buforin IIb | Genscript | 24 |
| 25 | Pep27 | Eurofins | 25 |
| 26 | 9R | Filgen | 26 |
| 27 | MG2A | Genscript | 27 |
| 28 | Short α-helical peptides (1) | Sigma | 28 |

TABLE 1-continued

| | | | |
|---|---|---|---|
| 29 | Defensin HNP-1 | Bachem | 29 |
| 30 | Cecropin B | Bachem | 30 |
| 31 | Histatin-5 | Bachem | 31 |
| 32 | Macropin 1 | Sigma | 32 |
| 33 | Tuftsin | Bachem | 33 |
| 34 | HHPHG | Filgen | 34 |
| 35 | (HHPHG) 2 | Filgen | 35 |
| 36 | (HHPHG) | Filgen | 36 |
| 37 | (HHPHG) 4 | Filgen | 37 |
| 38 | A3K | Genscript | 38 |
| 39 | PR-39 | Eurofins | 39 |
| 40 | A6K | Genscript | 40 |
| 41 | PTP7 | Genscript | 41 |
| 42 | Hepcidin TH2-3 | Sigma | 42 |
| 43 | A9K | Eurofins | 43 |
| 44 | Alloferon 1 | Genscript | 44 |
| 45 | Sesquin | Filgen | 45 |
| 46 | Gageostatin C | Filgen | 46 |
| 47 | PNC-28 | Filgen | 47 |
| 48 | C-Reactive Protein (CRP) (174-185) | Bachem | 48 |
| 49 | (Gln$^{53}$)-Connexin 37 (51-58) | Bachem | 49 |
| 50 | EP3 | Filgen | 50 |
| 51 | BERT II-1 | Genscript | 51 |
| 52 | Dermcidin 1L | Bachem | 52 |
| 53 | Hepcidin-20 | Bachem | 53 |
| 54 | 1% CTAB | — | — |
| 55 | 1% Benzalkonium-Cl | — | — |
| 56 | 4M quanidine | — | — |
| 57 | 100 μM Octadecylphosphophosphoniumcholine | Bachem | — |

| sample No. | Amino acid sequence |
|---|---|
| 1 | GIGKFLHASKKFGKAFVGEIMNS |
| 2 | IXXIXLXXPGXKXGALMGXNMKXAXXHXSINVXK |
| 3 | FKCRRWQWRMKKLGAPSITCVRRAF |
| 4 | LLGDFFRKSKEKIGKEFKRIVQRIKDFLRNLVPRTES |
| 5 | GIGAVLKVLTTGLPALISWIKRKRQQ |
| 6 | GIGKFLHSAKKFGKAFVGEIMNSGGQRLGNQWAVGHLM |
| 7 | GLLRKGGEKIGEKLKKIGQKIKNFFQKLVPQPEQ |
| 8 | GLLSVLGSVAKHVLPHVVPVIAEHL |
| 9 | GIGTKILGGVKTALKGALKELASTYAN |
| 10 | GIGTKILGGVKTALKGALKKELASTYAN |
| 11 | ALWKTMLKKLGTMALHAGKAALGAAADTISQGTQ |
| 12 | GLLQTIKEKLESLESLAKGIVSGIQA |
| 13 | GLFMIPGLIGGLISAFK |
| 14 | FRRKRKWLRRIGKGVKIIGGAALDHL |
| 15 | GFKDLLKGAAKALVKTVLF |
| 16 | IDWKKLLDAAKQIL |
| 17 | KILRGVCKKIMRTFLRRISKDILTGKK |
| 18 | GPIFHIIKGLFHAGKMIHGLV |
| 19 | GIIKKIIKKIIKKIIKKI |
| 20 | GFFALIPKIISSPLFKTLLSAVGSALSSSGGQE |
| 21 | RWGKWFKKATHVGKHVGKAALTAYL |
| 22 | LKLLKKLLKKLLKLL |
| 23 | GIGKFLHSAGKFGKAFVGEIMKS |
| 24 | RAGLQFPVGRLLRRLLRRLLR |
| 25 | MRKEFHNVLSSGQLLADKRPARDYNRK |
| 26 | RRRRRNWMWC |
| 27 | GIGKFLHSAKKFGKAFVGEIMNSGGKKWKMRRNQFWVKVQRG |
| 28 | KIIKKIIKKI |
| 29 | ACYCRIPACIAGERRYGTCIYQGRLWAFCC |
| 30 | KWKVFKKIEKMGRNIRNGIVKAGPAIAVLGEAKAL |
| 31 | DSHAKRHHGYKRKFHEKHHSHRGY |
| 32 | GFGMALKLLKKVL |
| 33 | TKPR |
| 34 | HHPHG |
| 35 | HHPHGHHPHG |
| 36 | HHPHGHHPHGHHPHG |
| 37 | HHPHGHHPHGHHPHGHHPGH |
| 38 | AAAK |
| 39 | RRRPRPPYLPRPRPPPPFFPPRLPPRIPPGFPPRFPPRFP |
| 40 | AAAAAAK |
| 41 | FLGALFKALSKLL |
| 42 | QSHLSLCRWCCNCCRSNKGC |
| 43 | AAAAAAAAAK |
| 44 | HGVSGHGQHGVHG |
| 45 | KTCENLADTY |
| 46 | LLDVLLE |
| 47 | ETFSDLWKLL |
| 48 | IYLGGPFSPNVL |

TABLE 1-continued

| | |
|---|---|
| 49 | FEQNTAQP |
| 50 | AMVGT |
| 51 | RDGDSCRGGGPV |
| 52 | SSLLEKGLDGAKKAVGGLGKLGKDAVEDLESVGKGAVHDVKDVLDSVL |
| 53 | ICIFCCGCCHRSKCGMCCKT |
| 54 | — |
| 55 | — |
| 56 | — |
| 57 | — |

| sample No. | Supplementary notes (present or absence of terminal modification, S—S bond, and the like) |
|---|---|
| 1 | — |
| 2 | 5 crosslinks present; CAS No. 1414-45-5 |
| 3 | S—S bond present (between Cys at the third position from the N terminal and Cys at the sixth position from the C terminal) |
| 4 | — |
| 5 | — |
| 6 | — |
| 7 | — |
| 8 | — |
| 9 | C-terminal amidation |
| 10 | — |
| 11 | — |
| 12 | — |
| 13 | C-terminal amidation |
| 14 | C-terminal amidation |
| 15 | — |
| 16 | C-terminal amidation |
| 17 | C-terminal amidation |
| 18 | C-terminal amidation |
| 19 | C-terminal amidation |
| 20 | — |
| 21 | C-terminal amidation |
| 22 | — |
| 23 | — |
| 24 | — |
| 25 | — |
| 26 | — |
| 27 | — |
| 28 | C-terminal amidation |
| 29 | 3 S—S bonds present (between Cys at the second position from the N-terminal and Cys at the first position from the C terminal, between Cys at the fourth position from the N terminal and Cys at the twelfth position from the C terminal, and between Cys at the position from the N terminal and Cys at the second position from the C terminal) |
| 30 | C-terminal amidation |
| 31 | — |
| 32 | C-terminal amidation |
| 33 | — |
| 34 | — |
| 35 | — |
| 36 | — |
| 37 | — |
| 38 | N-terminal acetylation and C-terminal amidation |
| 39 | — |
| 40 | N-terminal acetylation and C-terminal amidation |
| 41 | — |
| 42 | C-terminal amidation |
| 43 | N-terminal acetylation and C-terminal amidation |
| 44 | — |
| 45 | — |
| 46 | — |
| 47 | — |
| 48 | — |
| 49 | — |
| 50 | — |
| 51 | — |
| 52 | — |
| 53 | — |
| 54 | — |
| 55 | — |
| 56 | — |
| 57 | — |

TABLE 1-continued

| sample No. | Steric structure | Chain Length | Net charge | Ratio of hydrophobic residues | C | K | V | H | W | F | R |
|---|---|---|---|---|---|---|---|---|---|---|---|
| 1 | α-Helix | 23 | 3 | 43% | 0 | 4 | 1 | 1 | 0 | 3 | 0 |
| 2 | — | 34 | 3 | 44% | 5 | 3 | 1 | 2 | 0 | 0 | 0 |
| 3 | β-Sheet | 25 | 8 | 48% | 2 | 3 | 1 | 0 | 2 | 2 | 5 |
| 4 | α-Helix | 37 | 6 | 35% | 0 | 6 | 2 | 0 | 0 | 4 | 5 |
| 5 | α-Helix | 26 | 6 | 46% | 0 | 3 | 2 | 0 | 1 | 0 | 2 |
| 6 | — | 38 | 4.2 | 42% | 0 | 4 | 2 | 2 | 1 | 3 | 1 |
| 7 | Helix | 34 | 6 | 29% | 0 | 8 | 1 | 0 | 0 | 2 | 1 |
| 8 | Helix | 25 | 1 | 56% | 0 | 1 | 6 | 3 | 0 | 0 | 0 |
| 9 | Unknown | 27 | 3 | 40% | 0 | 4 | 1 | 0 | 0 | 0 | 0 |
| 10 | Helix | 27 | 3 | 51% | 0 | 4 | 2 | 0 | 0 | 0 | 0 |
| 11 | α-Helix | 34 | 3.1 | 50% | 0 | 4 | 0 | 1 | 1 | 0 | 0 |
| 12 | Unknown | 26 | 1 | 42% | 0 | 3 | 1 | 0 | 0 | 0 | 0 |
| 13 | Unknown | 17 | 1 | 58% | 0 | 1 | 0 | 0 | 0 | 2 | 0 |
| 14 | — | 26 | 9.1 | 38% | 0 | 4 | 1 | 1 | 1 | 0 | 5 |
| 15 | Helix | 19 | 4 | 57% | 0 | 4 | 2 | 0 | 0 | 2 | 0 |
| 16 | Helix | 14 | 2 | 57% | 0 | 3 | 0 | 0 | 1 | 0 | 0 |
| 17 | — | 27 | 9.9 | 40% | 1 | 6 | 1 | 0 | 0 | 1 | 4 |
| 18 | Unknown | 21 | 3 | 57% | 0 | 2 | 1 | 3 | 0 | 3 | 0 |
| 19 | α-Helix | 18 | 9 | 50% | 0 | 8 | 0 | 0 | 0 | 0 | 0 |
| 20 | Helix | 33 | 1 | 45% | 0 | 2 | 1 | 0 | 0 | 3 | 0 |
| 21 | — | 25 | 7.2 | 44% | 0 | 5 | 2 | 2 | 2 | 1 | 1 |
| 22 | — | 15 | 6 | 60% | 0 | 6 | 0 | 0 | 0 | 0 | 0 |
| 23 | α-Helix | 23 | 3.1 | 43% | 0 | 4 | 1 | 1 | 0 | 3 | 0 |
| 24 | α-Helix | 21 | 7 | 47% | 0 | 0 | 1 | 0 | 0 | 1 | 7 |
| 25 | Helix | 27 | 4 | 29% | 0 | 3 | 1 | 1 | 0 | 1 | 4 |
| 26 | — | 10 | 4.9 | 40% | 1 | 0 | 0 | 0 | 2 | 0 | 5 |
| 27 | — | 42 | 10.1 | 38% | 0 | 8 | 3 | 1 | 2 | 4 | 3 |
| 28 | α-Helix | 10 | 5 | 50% | 0 | 4 | 0 | 0 | 0 | 0 | 0 |
| 29 | β-Sheet | 30 | 3 | 53% | 6 | 0 | 0 | 0 | 1 | 1 | 4 |
| 30 | α-Helix | 35 | 7 | 48% | 0 | 7 | 3 | 0 | 1 | 1 | 2 |
| 31 | α-Helix | 24 | 5.7 | 8% | 0 | 4 | 0 | 7 | 0 | 1 | 3 |
| 32 | Helix | 13 | 4 | 61% | 0 | 3 | 1 | 0 | 0 | 1 | 0 |
| 33 | — | 4 | 2 | | 0 | 1 | 0 | 0 | 0 | 0 | 1 |
| 34 | — | 5 | 0.3 | 0% | 0 | 0 | 0 | 3 | 0 | 0 | 0 |
| 35 | — | 10 | 0.6 | 0% | 0 | 0 | 0 | 6 | 0 | 0 | 0 |
| 36 | — | 15 | 0.9 | 0% | 0 | 0 | 0 | 9 | 0 | 0 | 0 |
| 37 | — | 20 | 1.2 | 0% | 0 | 0 | 0 | 12 | 0 | 0 | 0 |
| 38 | — | 4 | 1 | | 0 | 1 | 0 | 0 | 0 | 0 | 0 |
| 39 | Rich | 39 | 11 | 20% | 0 | 0 | 0 | 0 | 0 | 5 | 10 |
| 40 | — | 7 | 1 | | 0 | 1 | 0 | 0 | 0 | 0 | 0 |
| 41 | — | 13 | 2 | 69% | 0 | 2 | 0 | 0 | 0 | 2 | 0 |
| 42 | — | 20 | 3.7 | 45% | 6 | 1 | 0 | 1 | 1 | 0 | 2 |
| 43 | — | 10 | 1 | | 0 | 1 | 0 | 0 | 0 | 0 | 0 |
| 44 | Rich | 13 | 0.4 | 15% | 0 | 0 | 2 | 4 | 0 | 0 | 0 |
| 45 | — | 10 | -1.1 | 30% | 1 | 1 | 0 | 0 | 0 | 0 | 0 |
| 46 | Unknown | 7 | -1 | 71% | 0 | 0 | 1 | 0 | 0 | 0 | 0 |
| 47 | — | 10 | -1 | 50% | 0 | 1 | 0 | 0 | 1 | 1 | 0 |
| 48 | — | 12 | 0 | 41% | 0 | 0 | 1 | 0 | 0 | 1 | 0 |
| 49 | — | 8 | -1 | 25% | 0 | 0 | 0 | 0 | 0 | 1 | 0 |
| 50 | Unknown | 5 | -1 | 60% | 0 | 0 | 1 | 0 | 0 | 0 | 0 |
| 51 | — | 12 | -0.1 | 16% | 1 | 0 | 1 | 0 | 0 | 0 | 2 |
| 52 | α-Helix | 48 | -1.9 | 39% | 0 | 7 | 7 | 1 | 0 | 0 | 0 |
| 53 | β-Sheet | 20 | 2.6 | 60% | 8 | 2 | 0 | 1 | 0 | 1 | 1 |
| 54 | — | — | — | — | 0 | 0 | 0 | 0 | 0 | 0 | 0 |
| 55 | — | — | — | — | — | — | — | — | — | — | — |
| 56 | — | — | — | — | — | — | — | — | — | — | — |
| 57 | — | — | — | — | — | — | — | — | — | — | — |

<Preparation of Exosome Sample>
(Exosome Fraction A Derived from Human Breast Cancer Cells)

Cell line MM 231-luc-D3H2LN derived from human breast cancer cells (provided by the National Cancer Center Research Institute) was inoculated into Advanced RPMI 1640 medium (manufactured by Life Technologies), followed by culturing at 37° C. for 48 hours under the condition that $CO_2$ concentration was set to 5 volume % using a $CO_2$ incubator, and therefore a culture solution containing exosomes was obtained. This culture solution was centrifuged at 2,000 G to remove the precipitate, followed by centrifugation at 110,000 G to precipitate the exosomes, and then an exosome fraction A was recovered. The recovered exosome fraction A was suspended in a phosphate buffered saline (PBS) and then stored at 4° C. Storage samples were lightly suspended with a vortex mixer (vibration mixer) before use.

In addition, the number of exosomes in the solution was analyzed using a nanoparticle analyzer (NanoSight LM10; manufactured by NanoSight, Ltd.) according to the protocol attached to the analyzer.

(Exosome Fraction B Derived from Human Breast Cancer Cells)

A cell suspension of cell line MDA-MB-231-luc-D3H2LN derived from human breast cancer (=MM231-luc-D3H2LN, provided by the National Cancer Center Research Institute) was seeded in a dish containing RPMI 1640 medium (manufactured by Thermo Fisher Scientific Inc.) containing 10% fetal bovine serum. Subsequently, the cell line was grown at 37° C. under the condition that $CO_2$ concentration was set to 5 volume % using a $CO_2$ incubator, and then the medium was replaced with Advanced RPMI 1640 medium (manufactured by Thermo Fisher Scientific Inc.), followed by culturing for 48 hours, and therefore the culture solution containing exosomes was obtained. This culture solution was centrifuged at 2,000 G for 10 minutes to remove the precipitate, followed by centrifugation at 110,000 G for 70 minutes to precipitate the exosomes, and therefore an exosome fraction B was recovered. The recovered exosome fraction B was suspended in a phosphate buffered saline (PBS) and then stored at 4° C. Storage samples were lightly suspended with a vortex mixer (vibration mixer) before use.

In addition, the number of exosomes in the solution was analyzed using the nanoparticle analyzer (NanoSight LM10; manufactured by NanoSight, Ltd.) according to the protocol attached to the analyzer.

(Exosome Fraction Derived from Human Mammary Epithelial Cells)

A cell suspension of cell line MCF 10A derived from human mammary epithelial cells (provided by the National Cancer Center Research Institute) was seeded in a dish containing Mammary Epithelium Cell Basal Medium (manufactured by Lonza). Subsequently, the cell line was grown at 37° C. under the condition that $CO_2$ concentration was set to 5 volume % using a $CO_2$ incubator, and then the medium was replaced with a fresh medium, followed by culturing for 48 hours, and the culture solution containing exosomes was obtained. This culture solution was centrifuged at 2,000 G for 10 minutes to remove the precipitate, followed by centrifugation at 110,000 G for 70 minutes to precipitate the exosomes, and an exosome fraction was recovered. The recovered exosome fraction was suspended in a phosphate buffered saline (PBS) and then stored at 4° C. Storage samples were lightly suspended with a vortex mixer (vibration mixer) before use.

The number of exosomes in the solution was analyzed using the nanoparticle analyzer (NanoSight LM10; manufactured by NanoSight, Ltd.) according to the protocol attached to the analyzer.

(Exosome Fraction Derived from Human Prostate Cancer Cells)

A cell suspension of cell line PC3ML derived from human prostate cancer cells (provided by the National Cancer Center Research Institute) was seeded in a dish containing RPMI 1640 medium (manufactured by Thermo Fisher Scientific Inc.) containing 10% fetal bovine serum. Subsequently, the cell line was grown at 37° C. under the condition that $CO_2$ concentration was set to 5 volume % using a $CO_2$ incubator, and then the medium was replaced with Advanced RPMI 1640 medium (manufactured by Thermo Fisher Scientific Inc.), followed by culturing for 48 hours, and the culture solution containing exosomes was obtained. This culture solution was centrifuged at 2,000 G for 10 minutes to remove the precipitate, followed by centrifugation at 110,000 G for 70 minutes to precipitate the exosomes, and therefore an exosome fraction was recovered. The recovered exosome fraction was suspended in a phosphate buffered saline (PBS) and then stored at 4° C. Storage samples were lightly suspended with a vortex mixer (vibration mixer) before use.

The number of exosomes in the solution was analyzed using the nanoparticle analyzer (NanoSight LM10; manufactured by NanoSight, Ltd.) according to the protocol attached to the analyzer.

(Exosome Fraction Derived from Normal Human Serum)

Pooled Human Serum (manufactured by Cosmo Bio Inc.) was centrifuged at 2,000 G for 10 minutes, and then the oil layer and the precipitate were removed, followed by centrifugation at 110,000 G for 70 minutes to precipitate the exosomes, and an exosome fraction was recovered. The recovered exosome fraction was suspended in a phosphate buffered saline (PBS) and then stored at 4° C. Storage samples were lightly suspended with a vortex mixer (vibration mixer) before use.

The number of exosomes in the solution was analyzed using the nanoparticle analyzer (NanoSight LM10; manufactured by NanoSight, Ltd.) according to the protocol attached to the analyzer.

<Quantitative Method for MicroRNA (Real-Time PCR Method)>

MicroRNA (miR-21 or miR-16) in the reaction solution was subjected to reverse transcription PCR using reverse transcription primers (manufactured by Thermo Fisher Scientific Inc., Taqman microRNA Assays, RT primers, and hsa-mir-21 or hsa-mir-16) and a reverse transcriptase (manufactured by Thermo Fisher Scientific Inc., Taqman microRNA RT kit).

The reverse transcription PCR solution obtained by the above described method was processed and by comparing the number of cycles on a calibration curve of microRNA using Taqman Assay primer (manufactured by Thermo Fisher Scientific Inc., Taqman microRNA Assays, Taqman Assay primer, and hsa-mir-21 or hsa-mir-16) and Real-Time PCR Master Mixes (manufactured by Thermo Fisher Scientific Inc., TaqMan Universal PCR Master Mix II, w/UNG) with StepOnePlus Real-Time PCR System, MiR-21 or miR-16 was quantified. The calibration curve of microRNA was created using synthetic miR-21 (manufactured by Sigma-Aldrich Co. LLC.) or synthetic miR-16 (manufactured by Sigma-Aldrich Co. LLC.).

Destruction of Exosome Using Magainin 2

Example 1

First, a phosphate buffered saline (PBS) solution of the exosome fraction A prepared from the cell line MM231-luc-D3H2LN derived from human breast cancer cells, the solution containing $1.36 \times 10^{11}$ particles/mL of the exosomes, and a PBS solution of 200 µM magainin 2 were prepared. Subsequently, 10 µL of the exosome solution derived from human breast cancer cells, 50 µL of magainin 2 solution, and 40 µL of PBS were mixed to prepare 100 µL of PBS containing $1.36 \times 10^{10}$ particles/mL of the exosomes derived from human breast cancer cells and 100 µM of magainin 2, followed by incubation by being left to stand at 25° C. for 24 hours. Samples were stored at 4° C.

Comparative Example 1

First, a phosphate buffered saline (PBS) solution of the exosome fraction A prepared from the cell line MM231-luc-D3H2LN derived from human breast cancer cells, the solution containing $1.36 \times 10^{11}$ particles/mL of the exosomes was prepared. Subsequently, 10 µL of the exosome solution derived from human breast cancer cells and 90 µL of PBS were mixed to prepare 100 µL of PBS containing $1.36 \times 10^{10}$ particles/mL of the exosomes derived from human breast cancer cells, followed by incubation by being left to stand at 25° C. for 24 hours. Samples were stored at 4° C.

The incubated solution was lightly suspended with a vortex mixer (vibration mixer), and then the number of exosomes in the solution was measured using the nanoparticle analyzer (NanoSight LM10; manufactured by NanoSight, Ltd.). In the solution of Example 1, the number of exosomes in the solution decreased to $1.89 \times 10^9$ particles/mL by allowing the antimicrobial peptide (magainin 2) to coexist with the exosomes. On the other hand, the number of exosomes was $1.36 \times 10^{10}$ particles/mL in the comparative example.

Selectivity of Magainin 2 Against Exosomes Derived from Human Breast Cancer Cells Example 2

The exosome fraction A prepared from the cell line MM231-luc-D3H2LN derived from human breast cancer cells was added to a peripheral blood sample collected from a healthy person with no cancer (hereinafter will be also referred to as human peripheral blood sample) so as to become an exosome concentration of an actual cancer patient, and thereby an artificial sample of a human peripheral blood of the cancer patient was produced. The human peripheral blood sample was obtained after procurement of the patient informed consent according to the Declaration of Helsinki, similarly to the method described in Japanese Unexamined patent publication No. 2013-198483, for example. Blood was drawn using a blood collection tube containing an anticoagulant.

Subsequently, the exosomes derived from human breast cancer cells pelleted by ultracentrifugation at 110,000 G, and magainin 2 were suspended in the human peripheral blood sample, and 100 μL of the human peripheral blood sample was prepared such that the content of the exosomes derived from human breast cancer cells and magainin 2 became $1.4 \times 10^{10}$ particles/mL of the exosomes derived from human breast cancer cells and 100 μM of magainin 2, respectively, and then incubated by being left to stand at 25° C. for 24 hours.

Comparative Example 2

The exosomes derived from human breast cancer cells pelleted by ultracentrifugation at 110,000 G, and phenol were suspended in the human peripheral blood sample, and 100 μL of the human peripheral blood sample was prepared such that the content of the exosomes derived from human breast cancer cells and phenol became $1.4 \times 10^{10}$ particles/mL of the exosomes derived from human breast cancer cells and 8% of phenol, respectively, and then incubated by being left to stand at 25° C. for 24 hours.

Comparative Example 3

The exosomes derived from human breast cancer cells pelleted by ultracentrifugation at 110,000 G was suspended in the human peripheral blood sample, and 100 μL of the human peripheral blood sample was prepared such that the content of the exosomes derived from human breast cancer cells became $1.4 \times 10^{10}$ particles/mL, and then incubated by being left to stand at 25° C. for 24 hours.

Using a part of the incubated solution, the exosomes were purified with Exo-Flow32 CD9 IP Kit (manufactured by SBI), and then the number of exosomes in the solution was measured using the nanoparticle analyzer (NanoSight LM10; manufactured by NanoSight, Ltd.). In Example 2 and Comparative Example 2, the exosome amount decreased compared to Comparative Example 3. In addition, a part of the incubated solution was subjected to the serum component protein electrophoresis. In Example 2 and Comparative Example 3, albumin components (molecular weight of 60 thousand to 70 thousand) and globulin components (molecular weight of approximately 160 thousand) did not decrease compared to Comparative Example 2.

Destruction of Exosome Using Nisin A, Lactoferricin, and LL-37

Example 3

First, a phosphate buffered saline (PBS) solution of the exosome fraction A derived from human breast cancer cells, the solution containing $1.36 \times 10^{11}$ particles/mL of the exosomes, and a PBS solution of 100 μM Nisin A were prepared. Subsequently, 10 μL of the exosome solution derived from human breast cancer cells, 50 μL of the Nisin A solution, and 40 μL of PBS were mixed to prepare 100 μL of the exosome fraction such that PBS contains $1.36 \times 10^{10}$ particles/mL of the exosomes derived from human breast cancer cells and 50 μM of Nisin A, followed by incubation by being left to stand at 25° C. for 48 hours. Samples were stored at 4° C. The incubated solution was lightly suspended with a vibration mixer, and then the number of exosomes in the solution was measured using the nanoparticle analyzer (NanoSight LM10; manufactured by NanoSight, Ltd.).

Example 4

First, a phosphate buffered saline (PBS) solution of the exosome fraction A derived from human breast cancer cells, the solution containing $1.36 \times 10^{11}$ particles/mL of the exosome, and a PBS solution of 100 μM lactoferricin were prepared. Subsequently, 10 μL of the solution of the exosomes derived from human breast cancer cells, 50 μL of the lactoferricin solution, and 40 μL of PBS were mixed to prepare 100 μL of the exosome fraction such that PBS contains $1.36 \times 10^{10}$ particles/mL of the exosomes derived from human breast cancer cells and 50 μM of lactoferricin, followed by incubation by being left to stand at 25° C. for 48 hours. Samples were stored at 4° C. The incubated solution was lightly suspended with a vibration mixer, and then the number of exosomes in the solution was measured using the nanoparticle analyzer (NanoSight LM10; manufactured by NanoSight, Ltd.).

Example 5

First, a phosphate buffered saline (PBS) solution of the exosome fraction A derived from human breast cancer cells, the solution containing $1.36 \times 10^{11}$ particles/mL of the exosomes, and a PBS solution of 100 μM LL-37 were prepared. Subsequently, 10 μL of the solution of the exosomes derived from human breast cancer cells, 50 μL of the LL-37 solution, and 40 μL of PBS were mixed to prepare 100 μL of PBS containing $1.36 \times 10^{10}$ particles/mL of the exosomes derived from human breast cancer cells and 50 μM of LL-37, followed by incubation by being left to stand at 25° C. for 48 hours. Samples were stored at 4° C. The incubated solution was suspended with a vibration mixer, and then the number of exosomes in the solution was measured using the nanoparticle analyzer (NanoSight LM10; manufactured by NanoSight, Ltd.).

Comparative Example 4

First, a phosphate buffered saline (PBS) solution of the exosome fraction A derived from human breast cancer cells, the solution containing $1.36 \times 10^{11}$ particles/mL of the exosomes was prepared. Subsequently, 10 µL of the solution of the exosomes derived from human breast cancer cells and 90 µL of PBS were mixed to prepare 100 µL of PBS containing $1.36 \times 10^{10}$ particles/mL of the exosomes derived from human breast cancer cells, followed by incubation by being left to stand at 25° C. for 48 hours. Samples were stored at 4° C. The incubated solution was lightly suspended with a vibration mixer, and then the number of exosomes in the solution was measured using the nanoparticle analyzer (NanoSight LM10; manufactured by NanoSight, Ltd.).

As a result of comparing the solution of Example 3 with the solution of Comparative Example 4, the number of exosomes in the solution decreased to $4.51 \times 10^9$ particles/mL in Example 3 by allowing the antimicrobial peptide to coexist with the exosomes. Similarly, as a result of comparing the solution of Example 4 with the solution of Comparative Example 4, the number of exosomes in the solution decreased to $7.47 \times 10^9$ particles/mL. As a result of comparing the solution of Example 5 with the solution of Comparative Example 4, the number of exosomes in the solution decreased to $1.09 \times 10^9$ particles/mL.

Effect of Immobilization on Carrier on Destruction of Exosome

Example 6

A PBS solution containing magainin 2 at a concentration of 500 µg/mL was prepared. Subsequently, 100 µL of the magainin 2 solution was brought into contact with 100 mg of Epoxy-activated Sepharose 6B carrier (manufactured by GE Healthcare) and reacted at room temperature for 24 hours. After washing the carrier three times with PBS, 100 µL of 1M ethanolamine (pH 8.0) was added thereto, followed by reaction at 40° C. for 4 hours. Thereafter, the carrier was washed three times with PBS to obtain Epoxy-activated Sepharose 6B carrying magainin 2. Next, a phosphate buffered saline (PBS) solution of the exosome fraction A derived from human breast cancer cells, the solution containing $9.92 \times 10^{10}$ particles/mL of the exosomes, was prepared, and 10 µL of the exosome derived from human breast cancer cells and 90 µL of PBS were mixed to prepare 100 µL of PBS containing $9.92 \times 10^9$ particles/mL of the exosomes derived from human breast cancer cells. Subsequently, this exosome fraction was brought into contact with the Epoxy-activated Sepharose 6B carrier carrying magainin 2, followed by incubation by being left to stand at 25° C. for 24 hours. The number of exosomes in the obtained eluate decreased to $5.68 \times 10^9$ particles/mL.

Example 7

A phosphate buffered saline (PBS) solution of the exosome fraction A derived from human breast cancer cells, the solution containing $1 \times 10^{11}$ particles/mL of the exosomes was prepared. Thereafter, 10 µL of the exosome derived from human breast cancer cells and 90 µL of PBS were mixed to prepare 100 µL of PBS containing $1 \times 10^{10}$ particles/mL of the exosomes derived from human breast cancer cells. Subsequently, 100 µL of the exosome fraction was brought into contact with Epoxy-activated Sepharose 6B carrier carrying magainin 2 and anti-human CD9 antibody (manufactured by Funakoshi Co., Ltd., PRO-485), followed by incubation by being left to stand at 25° C. for 24 hours. The number of exosomes in the obtained eluate decreased.

Example 8

A human blood sample containing $1 \times 10^{10}$ particles/mL of the exosome fraction A derived from human breast cancer cells was prepared. Subsequently, 100 µL of the human blood sample was brought into contact with Epoxy-activated Sepharose 6B carrier (manufactured by GE Healthcare) carrying magainin 2 and anti-human CD9 antibody (manufactured by Funakoshi Co., Ltd., PRO-485), followed by incubation by being left to stand at 25° C. for 24 hours. The number of exosomes in the obtained eluate decreased.

Example 9

A phosphate buffered saline (PBS) solution of the exosome fraction A derived from human breast cancer cells, the solution containing $1 \times 10^{11}$ particles/mL of the exosomes was prepared. Thereafter, 10 µL of the exosome derived from human breast cancer cells and 90 µL of PBS were mixed to prepare 100 µL of PBS containing $1 \times 10^{10}$ particles/mL of the exosomes derived from human breast cancer cells. Subsequently, 100 µL of the human blood sample was brought into contact with Epoxy-activated Sepharose 6B carrier (manufactured by GE Healthcare) carrying magainin 2 and Epoxy-activated Sepharose 6B carrier carrying anti-human CD9 antibody (manufactured by Funakoshi Co., Ltd., PRO-485), followed by incubation by being left to stand at 25° C. for 24 hours. The number of exosomes in the obtained eluate decreased.

Reference Example

<Effect of Addition of RNase Inhibitor on Stability of MicroRNA>

10 µL of the exosome fraction was prepared such that PBS contains $1 \times 10^{10}$ particles/mL of the exosome fraction B derived from human breast cancer cells, $1 \times 10^{-13}$M of miR-21 (manufactured by Sigma-Aldrich Co. LLC.), and 0.4 U/µL of RNase inhibitor (manufactured by Toyobo Co., Ltd.), followed by incubation by being left to stand at 37° C. for 24 hours.

Comparative Example 5

10 µL of the exosome fraction was prepared such that PBS contains $1 \times 10^{10}$ particles/mL of the exosome fraction B derived from human breast cancer cells, and $1 \times 10^{-13}$M of miR-21 (manufactured by Sigma-Aldrich Co. LLC.), followed by incubation by being left to stand at 37° C. for 24 hours.

The amount of microRNA in the above reference example and Comparative Example 5 was quantified by the above described real-time PCR method, and no decrease in the microRNA concentration was shown in the reference example including the RNase inhibitor, but the microRNA concentration decreased to $6 \times 10^{15}$M in Comparative Example 5.

Extraction of MicroRNA from Exosomes Derived from Human Breast Cancer Cells

Example 10

10 μL of the exosome fraction was prepared such that PBS contains 1×10$^{11}$ particles/mL of the exosome fraction B derived from human breast cancer cells, various antimicrobial peptides shown in the following Table 2 adjusted to 100 μM, and 0.4 U/μL of RNase inhibitor (manufactured by Toyobo Co., Ltd.), followed by incubation by being left to stand at 37° C. for 24 hours.

Comparative Example 6

10 μL of the exosome fraction was prepared such that PBS contains 1×10$^{11}$ particles/mL of the exosome fraction B derived from human breast cancer cells, and 0.4 U/μL of RNase inhibitor (manufactured by Toyobo Co., Ltd.), followed by incubation by being left to stand at 37° C. for 24 hours.

MicroRNA eluted into the solution was purified and recovered from the incubated solution of Example 10 above and Comparative Example 6 above by the following method.

First, 160 μL of PBS was added to the reaction solution, and then the solution was added to a centrifugal filter (manufactured by Millipore Corporation, Amicon Ultra 0.5 mL, 100K filter) and centrifuged at 14,000 G for 2 minutes. Subsequently, 100 μL of the centrifuged filtrate was recovered and introduced into a 1.5 mL tube. Next, 350 μL of RLT buffer (manufactured by QIAGEN, attached with RNeasy mini kit) and 675 μL of ethanol were added and mixed in the 1.5 mL tube. The obtained mixture was separated into two parts, and each of the separates was added onto a spin column (manufactured by QIAGEN, attached with RNeasy mini kit) followed by centrifugation at 8,000 G for 15 seconds, and the entire amount of the mixture was passed through the spin column. Thereafter, 500 μL of RPE buffer (manufactured by QIAGEN, attached with RNeasy mini kit) was added thereto and centrifuged at 8,000 G for 15 seconds. Furthermore, 500 μL of the RPE buffer was added to the spin column once more and centrifuged at 8,000 G for 15 seconds. Thereafter, the spin column was centrifuged at 14,000 G for 1 minute to remove the residual RPE buffer. Next, 30 μL of RNase free water (manufactured by QIAGEN, attached with RNeasy mini kit) was added to the spin column, left for 1 minute, and then centrifuged at 14,000 G for 1 minute, and the eluate obtained thereby was recovered.

The amount of microRNA (miR-21) contained in the eluate recovered by the above described method was quantified by the above described real-time PCR method. As a result, the extraction of microRNA was confirmed in several peptides by treating the exosomes with the antimicrobial peptide. In addition, the destructive activity of the antimicrobial peptide used was evaluated on the basis of the following criteria based on the quantitative result of the concentration of microRNA (miR-21) performed by the real-time PCR method. The results are shown in the following Table 2. The solution of Comparative Example 6 incubated without using the antimicrobial peptide was treated by the above described method, and the amount of microRNA (miR-21) contained in the obtained eluate was quantified. As a result, the concentration of microRNA contained in the eluate was 8×10$^{-14}$M.

A: the concentration of microRNA is 50×10$^{-14}$M or more
B: the concentration of microRNA is 10×10$^{-14}$M to 50×10$^{-14}$M
D: the concentration of microRNA is less than 10×10$^{-14}$M

TABLE 2

| sample No. | Name of antimicrobial peptide | Destructive activity |
|---|---|---|
| 1 | Magainin 2 | A |
| 4 | LL-37 | A |
| 5 | Melittin | A |
| 6 | MG2B | A |
| 7 | mCRAMP | A |
| 8 | Caerin 1.1 | A |
| 9 | Maximin 1 | B |
| 10 | Maximin 4 | B |
| 11 | Dermaseptin | B |
| 12 | Maculatin 3.1 | B |
| 13 | TsAP-2 | B |
| 14 | NRC-03 | B |
| 15 | Ascaphin-8 | B |
| 16 | Polybia-MPI | B |
| 17 | NK-2 | B |
| 18 | Epinecidin-1 | B |
| 19 | Short α-helical peptides (2) | B |
| 20 | Pardaxin 4 | B |
| 21 | NRC-07 | B |
| 22 | K6L9 | B |
| 23 | Megainin I | B |
| 24 | Buforin IIb | B |
| 25 | Pep27 | B |
| 26 | 9R | B |
| 27 | MG2A | B |
| 28 | Short α-helical peptides (1) | B |
| 29 | Defensin HNP-1 | B |
| 30 | Cecropin B | B |
| 31 | Histatin-5 | B |
| 32 | Macropin 1 | B |
| 33 | Tuftsin | B |
| 34 | HHPHG | B |
| 35 | (HHPHG)2 | B |
| 36 | (HHPHG)3 | B |
| 37 | (HHPHG)4 | B |
| 38 | A3K | D |
| 39 | PR-39 | D |
| 40 | A6K | D |
| 41 | PTP7 | D |
| 42 | Hepcidin TH2-3 | D |
| 43 | A9K | D |
| 44 | Alloferon 1 | D |
| 45 | Sesquin | D |
| 46 | Gageostatin C | D |
| 47 | PNC-28 | D |
| 48 | C-Reactive Protein (CRP) (174-185) | D |
| 49 | (Gln$^{53}$)-Connexin 37(51-58) | D |
| 50 | EP3 | D |
| 51 | BEPT II-1 | D |
| 52 | Dermcidin-1L | D |
| 53 | Hepcidin-20 | D |
| 54 | 1% CTAB | D |
| 55 | 1% Benzalkonium-Cl | D |
| 56 | 4M guanidine | D |
| 57 | 100 μM Octadecylphosphophosphoniumcholine | D |

Extraction of MicroRNA from Exosome Derived from Prostate Cancer Cells

Example 11

10 μL of the exosome fraction was prepared such that PBS contains 1×10$^{11}$ particles/mL of the exosome derived from human prostate cancer cells (PC3ML), various antimicrobial peptides shown in the following Table 3 adjusted to 100 μM, and 0.4 U/μL of RNase inhibitor (manufactured by Toyobo Co., Ltd.), followed by incubation by being left to stand at 37° C. for 24 hours.

Comparative Example 7

10 μL of the exosome fraction was prepared such that PBS contains 1×10$^{11}$ particles/mL of the exosome derived from human prostate cancer cells (PC3ML), and 0.4 U/μL of RNase inhibitor (manufactured by Toyobo Co., Ltd.), followed by incubation by being left to stand at 37° C. for 24 hours.

The eluted MicroRNA was purified and recovered from the incubated solution of Example 11 above and Comparative Example 7 above by the same method as the above described method for extraction from the incubated solution of Example 10 above and Comparative Example 6 above.

The amount of microRNA (miR-21) contained in the recovered eluate was quantified by the above described real-time PCR method. As a result, the extraction of microRNA was confirmed in several peptides by treating the exosomes with the antimicrobial peptide. In addition, the destructive activity of the antimicrobial peptide used was evaluated on the basis of the following criteria based on the quantitative result of the concentration of microRNA (miR-21) performed by the real-time PCR method. The results are shown in the following Table 3. The solution of Comparative Example 7 incubated without using the antimicrobial peptide was treated by the above described method, and the amount of microRNA (miR-21) contained in the obtained eluate was quantified. As a result, the concentration of microRNA contained in the eluate was 3×10$^{-14}$M.

A: the concentration of microRNA is 10×10$^{-14}$M or more
B: the concentration of microRNA is 5×10$^{-14}$M to 10×10$^{-14}$M
D: the concentration of microRNA is less than 5×10$^{-14}$M

TABLE 3

| sample No. | Name of antimicrobial peptide | Destructive activity |
|---|---|---|
| 1 | Magainin 2 | B |
| 16 | Polybia-MPI | A |
| 22 | K6L9 | A |
| 52 | BEPT II-1 | D |

Selectivity of Various Antimicrobial Peptides Against Exosome Derived from Human Breast Cancer Cells Example 12

10 μL of the exosome fraction was prepared such that PBS contains 1×10$^{11}$ particles/mL of the exosome fraction B derived from human breast cancer cells, various antimicrobial peptides shown in the following Table 4 adjusted to 100 μM, and 0.4 U/μL of RNase inhibitor (manufactured by Toyobo Co., Ltd.), followed by incubation by being left to stand at 37° C. for 24 hours.

Thereafter, the eluted MicroRNA (miR-16) was purified and recovered from the incubated solution by the same method as the above described method for extraction from the incubated solution of Examples 10 and 11 above and Comparative Examples 6 and 7 above.

In addition, 10 μL of the exosome fraction was prepared such that PBS contains 1×10$^{11}$ particles/mL of an exosome fraction derived from human mammary gland cells (MCF-10A, normal cells), various antimicrobial peptides shown in the following Table 4 adjusted to 100 μM, and 0.4 U/μL of RNase inhibitor (manufactured by Toyobo Co., Ltd.), followed by incubation by being left to stand at 37° C. for 24 hours.

Thereafter, the eluted MicroRNA (miR-16) was purified and recovered from the incubated solution by the same method as the above described method for extraction from the incubated solution of Examples 10 and 11 above and Comparative Examples 6 and 7 above.

Comparative Example 8

10 μL of the exosome fraction was prepared such that PBS contains 1×10$^{11}$ particles/mL of the exosome fraction B derived from human breast cancer cells, and 0.4 U/μL of RNase inhibitor (manufactured by Toyobo Co., Ltd.), followed by incubation by being left to stand at 37° C. for 24 hours.

Thereafter, the eluted MicroRNA (miR-16) was purified and recovered from the incubated solution by the same method as the above described method for extraction from the incubated solution of Examples 10 and 11 above and Comparative Examples 6 and 7 above.

In addition, 10 μL of the exosome fraction was prepared such that PBS contains 1×10$^{11}$ particles/mL of the exosome fraction derived from human mammary gland cells (MCF-10A, normal cells), and 0.4 U/μL of RNase inhibitor (manufactured by Toyobo Co., Ltd.), followed by incubation by being left to stand at 37° C. for 24 hours.

Thereafter, the eluted MicroRNA (miR-16) was purified and recovered from the incubated solution by the same method as the above described method for extraction from the incubated solution of Examples 10 and 11 above and Comparative Examples 6 and 7 above.

Next, the amount of microRNA (miR-16) contained in each recovered eluate was quantified by the above described real-time PCR method. Subsequently, from the obtained quantitative results, a ratio of miR-16 for each antimicrobial peptide used was calculated by the following Formula 1. In addition, the selectivity of the antimicrobial peptide used in Example 12 was evaluated as "B" in a case where the calculated miR-16 value was higher than the miR-16 ratio of Comparative Example 8. The results are shown in the following Table 4.

miR-16 ratio={(quantitative value of microRNA (miR-16) contained in the eluate recovered from each incubated solution of Example 12 containing the exosomes derived from human breast cancer cells)−(quantitative value of microRNA (miR-16) contained in the eluate recovered from the incubated solution of Comparative Example 8 containing the exosomes derived from human breast cancer cells)}/{(quantitative value of microRNA (miR-16) contained in the eluate recovered from each incubated solution of Example 12 containing the exosomes derived from normal cells)−(quantitative value of microRNA (miR-16) contained in the eluate recovered from the incubated solution of Comparative Example 8 containing the exosomes derived from normal cells)}   Formula 1:

TABLE 4

| sample No. | Name of antimicrobial peptide | mir-16 ratio | Selectivity |
|---|---|---|---|
| 1 | Magainin 2 | 26 | B |
| 4 | LL-37 | 18 | B |

TABLE 4-continued

| sample No. | Name of antimicrobial peptide | mir-16 ratio | Selectivity |
|---|---|---|---|
| 5 | Melittin | 42 | B |
| 6 | MG2B | 22 | B |
| 7 | mCRAMP | 9 | B |
| 8 | Caerin 1.1 | 27 | B |
| 9 | Maximin 1 | 22 | B |
| 10 | Maximin 4 | 311 | B |
| — | No peptide | 0.6 | D |

As can be seen from Table 4 above, each of the antimicrobial peptides used in Example 12 enables selective destruction of the exosomes derived from human breast cancer cells.

<Comparison of Selectivity of Various Antimicrobial Peptide Against Antibody Specific to Cancer Cells>

(Preparation of Antibody)

40 μL of a suspension of EpCAM-exosome isolation reagent (manufactured by Thermo Fisher Scientific Inc.) was dispensed into a 1.5 mL tube, and after isolating the suspension with Magnetic Beads Separator (manufactured by Thermo Fisher Scientific Inc.), the pellet was recovered by removing the supernatant. 0.5 mL of PBS was added to this pellet and suspended, and after the obtained suspension was separated with the Magnetic Beads Separator, the pellet was recovered by removing the supernatant. Subsequently, the obtained pellet was mixed with 10 μL of $1.8\times10^{11}$ particles/mL of the exosomes derived from breast cancer cells (MM231-luc-D3H2LN) or $1.8\times10^{11}$ particles/mL of the exosomes derived from normal human serum, and then left at 4° C. for 18 hours. Next, after the mixture was separated with the Magnetic Beads Separator, the pellet was recovered by removing the supernatant. Thereafter, 1 mL of PBA was added to the pellet and suspended, and was separated with the Magnetic Beads Separator, and then the pellet was recovered by removing the supernatant. The operation of adding 1 mL of PBS and isolating the resultant was repeated once more. Thereafter, 10 μL of PBS was added to the obtained pellet and suspended, and therefore an antibody sample to which exosome was adsorbed was obtained.

Example 13

10 μL of the exosome fraction was prepared such that PBS contains $1\times10^{11}$ particles/mL of the exosome fraction B derived from human breast cancer cells, magainin 2 adjusted to 100 μM, and 0.4 U/μL of RNase inhibitor (manufactured by Toyobo Co., Ltd.), followed by incubation by being left to stand at 37° C. for 24 hours.

Thereafter, the eluted MicroRNA (miR-16) was purified and recovered from the incubated solution by the same method as the above described method for extraction from the incubated solution of Examples 10 to 12 above and Comparative Examples 6 to 8 above.

In addition, 10 μL of the exosome fraction was prepared such that PBS contains $1\times10^{11}$ particles/mL of the exosome fraction derived from normal human serum (normal cells), magainin 2 adjusted to 100 μM, and 0.4 U/μL of RNase inhibitor (manufactured by Toyobo Co., Ltd.), followed by incubation by being left to stand at 37° C. for 24 hours.

Thereafter, the eluted MicroRNA (miR-16) was purified and recovered from the incubated solution by the same method as the above described method for extraction from the incubated solution of Examples 10 to 12 above and Comparative Examples 6 to 8 above.

Comparative Example 9

10 μL of the exosome fraction of the antibody obtained by adsorbing the exosome fraction B derived from human breast cancer cells to the EpCAM-exosome isolation reagent was prepared and subjected to the extraction treatment using RNeasy kit, and therefore microRNA (miR-16) was purified and recovered.

Specifically, 350 μL of RLT buffer (manufactured by QIAGEN, attached with RNeasy mini kit) and 675 μL of ethanol were mixed in a 1.5 mL tube as a surfactant composition for exosome destruction. The obtained mixture was separated into two parts, and each of the separates was added onto a spin column (manufactured by QIAGEN, attached with RNeasy mini kit) followed by centrifugation at 8,000 G for 15 seconds, and the entire amount of the mixture was passed through the spin column. 500 μL of RPE buffer (manufactured by QIAGEN, attached with RNeasy mini kit) was added to the spin column and centrifuged at 8,000 G for 15 seconds. Furthermore, 500 μL of the RPE buffer was added to the spin column once more and centrifuged at 8,000 G for 15 seconds. The spin column was centrifuged at 14,000 G for 1 minute to remove the residual RPE buffer. 30 μL of RNase free water (manufactured by QIAGEN, attached with RNeasy mini kit) was added to the spin column, left for 1 minute, and then centrifuged at 14,000 G for 1 minute, and therefore the eluate containing microRNA (miR-16) was recovered.

10 μL of the exosome fraction of the antibody obtained by adsorbing the exosomes derived from normal human serum (normal cells) to the EpCAM-exosome isolation reagent was prepared and subjected to the extraction treatment using RNeasy kit by the method same as described above, and therefore microRNA (miR-16) was purified and recovered.

Thereafter, the eluted MicroRNA (miR-16) was purified from the incubated solution and recovered by the same method as the above described method for extraction from the incubated solution of Examples 10 to 12 above and Comparative Examples 6 to 8 above.

Comparative Example 10

The solution containing microRNA (miR-16) was purified and recovered from 10 μL of $1\times10^{11}$ particles/mL of the exosome fraction B derived from human breast cancer cells by the same method as that of Comparative Example 9. In addition, the solution containing microRNA (miR-16) was purified and recovered from 10 μL of $1\times10^{11}$ particles/mL of the exosome fraction derived from normal human serum by the same method as that of Comparative Example 9.

Comparative Example 11

10 μL of the exosome fraction was prepared such that PBS contains $1\times10^{11}$ particles/mL of the exosome fraction B derived from human breast cancer cells, and 0.4 U/μL of RNase inhibitor (manufactured by Toyobo Co., Ltd.), followed by incubation by being left to stand at 37° C. for 24 hours.

Thereafter, the eluted MicroRNA (miR-16) was purified and recovered from the incubated solution by the same method as the above described method for extraction from the incubated solution of Examples 10 to 12 above and Comparative Examples 6 to 8 above.

In addition, 10 μL of the exosome fraction was prepared such that PBS contains 1×10$^{11}$ particles/mL of the exosome fraction derived from normal human serum, and 0.4 U/μL of RNase inhibitor (manufactured by Toyobo Co., Ltd.), followed by incubation by being left to stand at 37° C. for 24 hours.

Thereafter, the eluted MicroRNA (miR-16) was purified and recovered from the incubated solution by the same method as the above described method for extraction from the incubated solution of Examples 10 to 12 above and Comparative Examples 6 to 8 above.

Next, the amount of microRNA (miR-16) contained in each recovered eluate was quantified by the above described real-time PCR method. Subsequently, from the obtained quantitative results, a ratio of miR-16 for each antimicrobial peptide used was calculated by the following formula. The results are shown in the following Table 5.

miR-16 ratio={(quantitative value of microRNA (miR-16) contained in the eluate recovered from each incubated solution of Example 13, Comparative Example 9 or 10 containing the exosomes derived from human breast cancer cells)−(quantitative value of microRNA (miR-16) contained in the eluate recovered from the incubated solution of Comparative Example 11 containing the exosomes derived from human breast cancer cells)}/{(quantitative value of microRNA (miR-16) contained in the eluate recovered from each incubated solution of Example 13, Comparative Example 9 or 10 containing the exosomes derived from normal cells)−(quantitative value of microRNA (miR-16) contained in the eluate recovered from the incubated solution of Comparative Example 11 containing the exosomes derived from normal cells)}     Formula 2:

TABLE 5

| sample No. | Name of antimicrobial peptide | mir-16 ratio | Selectivity |
|---|---|---|---|
| 1 | Magainin 2 | 56.6 | B |
| — | anti-EpCAM antibody | 7.7 | C |
| — | Surfactant composition | 0.7 | D |
| — | No peptide | 0.6 | D |

As can be seen from Table 5 above, the method for Example 13 using the antimicrobial peptide enables selective destruction of the exosomes derived from human breast cancer cells compared to the method for the comparative example not using the antimicrobial peptide.

This application claims priority based on Japanese Patent Application No. 2015-049136 filed on Mar. 12, 2015, the disclosure of which is incorporated herein in its entirety.

The invention claimed is:

1. A method for destroying exosomes, comprising:
   a step of preparing an antimicrobial peptide; and
   a step of allowing the antimicrobial peptide to coexist with the exosome to destroy the exosome.

2. The method for destroying exosomes according to claim 1,
   wherein the exosome is an exosome derived from cancer cells.

3. The method for destroying exosomes according to claim 1,
   wherein the exosome is a mixture of the exosome derived from cancer cells and an exosome derived from normal cells, and
   the step of destroying exosomes comprises selectively destroying the exosome derived from cancer cells.

4. The method for destroying exosomes according to claim 1, wherein the antimicrobial peptide is a peptide satisfying the following condition (1) or (2):
(1) the peptide has a chain length of 10 or more and less than 50, a net charge of more than 0 and less than 15, and a ratio of hydrophobic residues of 25% or more and less than 65% (excluding a peptide containing 3 or more S—S bonds, and containing any one of a lysine residue or a valine residue in total amino acids constituting the antimicrobial peptide);
(2) the peptide has a chain length of 2 or more and less than 10, a net charge of 0 or less, and a ratio of hydrophobic residues of less than 25%, and satisfies the following condition (2-1) or (2-2):
 (2-1) 3 or more histidine residues are contained and none of a tryptophan residue or a valine residue is contained in the total amino acids constituting the antimicrobial peptide;
 (2-2) 1 or more arginine residues are contained and none of a phenylalanine residue, a tryptophan residue, or a valine residue is contained in the total amino acids constituting the antimicrobial peptide.

5. The method for destroying exosomes according to claim 4,
wherein the antimicrobial peptide is a peptide satisfying the following condition:
(Condition) the peptide has a chain length of 20 or more and less than 40, a net charge of 1 or more and less than 10, and a ratio of hydrophobic residues of 25% or more and less than 65% (excluding a peptide containing 3 or more S—S bonds, and containing any one of a lysine residue or a valine residue in total amino acids constituting the antimicrobial peptide).

6. A method for isolating exosomes derived from normal cells, comprising:
a step of allowing an antimicrobial peptide satisfying the following condition (1) or (2) to coexist with an exosome,
wherein the exosome is a mixture of an exosome derived from cancer cells and an exosome derived from normal cells:
(1) the peptide has a chain length of 10 or more and less than 50, a net charge of more than 0 and less than 15, and a ratio of hydrophobic residues of 25% or more and less than 65% (excluding a peptide containing 3 or more S—S bonds, and containing any one of a lysine residue or a valine residue in total amino acids constituting the antimicrobial peptide);
(2) the peptide has a chain length of 2 or more and less than 10, a net charge of 0 or less, and a ratio of hydrophobic residues of less than 25%, and satisfies the following condition (2-1) or (2-2):
 (2-1) 3 or more histidine residues are contained and none of a tryptophan residue or a valine residue is contained in the total amino acids constituting the antimicrobial peptide;
 (2-2) 1 or more arginine residues are contained and none of a phenylalanine residue, a tryptophan residue, or a valine residue is contained in the total amino acids constituting the antimicrobial peptide.

7. The method for isolating exosomes derived from normal cells according to claim 6,
wherein the step of allowing coexistence comprises a step of destroying the exosome derived from cancer cells,
the method further comprising a step of adsorptive removal of a destruction residue of the exosome derived from cancer cells after the step of allowing coexistence.

* * * * *

SEQUENCE LISTING

```
<160> NUMBER OF SEQ ID NOS: 53

<210> SEQ ID NO 1
<211> LENGTH: 23
<212> TYPE: PRT
<213> ORGANISM: Artificial Sequence
<220> FEATURE:
<223> OTHER INFORMATION: Synthetic antibacterial peptide derived from
      Xenopus laevis

<400> SEQUENCE: 1

Gly Ile Gly Lys Phe Leu His Ser Ala Lys Lys Phe Gly Lys Ala Phe
1               5                   10                  15

Val Gly Glu Ile Met Asn Ser
            20

<210> SEQ ID NO 2
<211> LENGTH: 34
<212> TYPE: PRT
<213> ORGANISM: Artificial Sequence
<220> FEATURE:
<223> OTHER INFORMATION: Antibacterial peptide, containing five
      cross-linking bonds derived from Lactococcus lactis
<220> FEATURE:
<221> NAME/KEY: MISC_FEATURE
<222> LOCATION: (2)..(2)
<223> OTHER INFORMATION: Xaa is Dhb
<220> FEATURE:
<221> NAME/KEY: MISC_FEATURE
<222> LOCATION: (3)..(3)
<223> OTHER INFORMATION: Xaa is Lan
<220> FEATURE:
<221> NAME/KEY: MISC_FEATURE
<222> LOCATION: (5)..(5)
<223> OTHER INFORMATION: Xaa is Dha
<220> FEATURE:
<221> NAME/KEY: MISC_FEATURE
<222> LOCATION: (7)..(7)
<223> OTHER INFORMATION: Xaa is Lan
<220> FEATURE:
<221> NAME/KEY: MISC_FEATURE
<222> LOCATION: (8)..(8)
```

```
<223> OTHER INFORMATION: Xaa is Abu
<220> FEATURE:
<221> NAME/KEY: MISC_FEATURE
<222> LOCATION: (11)..(11)
<223> OTHER INFORMATION: Xaa is Lan
<220> FEATURE:
<221> NAME/KEY: MISC_FEATURE
<222> LOCATION: (13)..(13)
<223> OTHER INFORMATION: Xaa is Abu
<220> FEATURE:
<221> NAME/KEY: MISC_FEATURE
<222> LOCATION: (19)..(19)
<223> OTHER INFORMATION: Xaa is Lan
<220> FEATURE:
<221> NAME/KEY: MISC_FEATURE
<222> LOCATION: (23)..(23)
<223> OTHER INFORMATION: Xaa is Abu
<220> FEATURE:
<221> NAME/KEY: MISC_FEATURE
<222> LOCATION: (25)..(25)
<223> OTHER INFORMATION: Xaa is Abu
<220> FEATURE:
<221> NAME/KEY: MISC_FEATURE
<222> LOCATION: (26)..(26)
<223> OTHER INFORMATION: Xaa is Lan
<220> FEATURE:
<221> NAME/KEY: MISC_FEATURE
<222> LOCATION: (28)..(28)
<223> OTHER INFORMATION: Xaa is Lan
<220> FEATURE:
<221> NAME/KEY: MISC_FEATURE
<222> LOCATION: (33)..(33)
<223> OTHER INFORMATION: Xaa is Dha

<400> SEQUENCE: 2

Ile Xaa Xaa Ile Xaa Leu Xaa Xaa Pro Gly Xaa Lys Xaa Gly Ala Leu
1               5                   10                  15

Met Gly Xaa Asn Met Lys Xaa Ala Xaa Xaa His Xaa Ser Ile His Val
            20                  25                  30

Xaa Lys

<210> SEQ ID NO 3
<211> LENGTH: 25
<212> TYPE: PRT
<213> ORGANISM: Artificial Sequence
<220> FEATURE:
<223> OTHER INFORMATION: Synthetic peptide, containing one S-S bond
      derived from Bos taurus

<400> SEQUENCE: 3

Phe Lys Cys Arg Arg Trp Gln Trp Arg Met Lys Lys Leu Gly Ala Pro
1               5                   10                  15

Ser Ile Thr Cys Val Arg Arg Ala Phe
            20                  25

<210> SEQ ID NO 4
<211> LENGTH: 37
<212> TYPE: PRT
<213> ORGANISM: Artificial Sequence
<220> FEATURE:
<223> OTHER INFORMATION: Synthetic antibacterial peptide derived from
      Homo sapiens

<400> SEQUENCE: 4

Leu Leu Gly Asp Phe Phe Arg Lys Ser Lys Glu Lys Ile Gly Lys Glu
1               5                   10                  15

Phe Lys Arg Ile Val Gln Arg Ile Lys Asp Phe Leu Arg Asn Leu Val
            20                  25                  30

Pro Arg Thr Glu Ser
```

-continued

```
<210> SEQ ID NO 5
<211> LENGTH: 26
<212> TYPE: PRT
<213> ORGANISM: Artificial Sequence
<220> FEATURE:
<223> OTHER INFORMATION: Synthetic antibacterial peptide derived from
      Apis mellifera

<400> SEQUENCE: 5

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 6
<211> LENGTH: 38
<212> TYPE: PRT
<213> ORGANISM: Artificial Sequence
<220> FEATURE:
<223> OTHER INFORMATION: Synthetic antibacterial peptide

<400> SEQUENCE: 6

Gly Ile Gly Lys Phe Leu His Ser Ala Lys Lys Phe Gly Lys Ala Phe
1               5                   10                  15

Val Gly Glu Ile Met Asn Ser Gly Gly Gln Arg Leu Gly Asn Gln Trp
            20                  25                  30

Ala Val Gly His Leu Met
        35

<210> SEQ ID NO 7
<211> LENGTH: 34
<212> TYPE: PRT
<213> ORGANISM: Artificial Sequence
<220> FEATURE:
<223> OTHER INFORMATION: Synthetic antibacterial peptide derived from
      Mus musculus

<400> SEQUENCE: 7

Gly Leu Leu Arg Lys Gly Gly Glu Lys Ile Gly Glu Lys Leu Lys Lys
1               5                   10                  15

Ile Gly Gln Lys Ile Lys Asn Phe Phe Gln Lys Leu Val Pro Gln Pro
            20                  25                  30

Glu Gln

<210> SEQ ID NO 8
<211> LENGTH: 25
<212> TYPE: PRT
<213> ORGANISM: Artificial Sequence
<220> FEATURE:
<223> OTHER INFORMATION: Synthetic antibacterial peptide derived from
      Litoria splendida

<400> SEQUENCE: 8

Gly Leu Leu Ser Val Leu Gly Ser Val Ala Lys His Val Leu Pro His
1               5                   10                  15

Val Val Pro Val Ile Ala Glu His Leu
            20                  25

<210> SEQ ID NO 9
<211> LENGTH: 27
<212> TYPE: PRT
<213> ORGANISM: Artificial Sequence
```

```
<220> FEATURE:
<223> OTHER INFORMATION: Synthetic antibacterial peptide, c-terminus
      amidated dervied from Bombina maxima

<400> SEQUENCE: 9

Gly Ile Gly Thr Lys Ile Leu Gly Gly Val Lys Thr Ala Leu Lys Gly
1               5                   10                  15

Ala Leu Lys Glu Leu Ala Ser Thr Tyr Ala Asn
            20                  25

<210> SEQ ID NO 10
<211> LENGTH: 27
<212> TYPE: PRT
<213> ORGANISM: Artificial Sequence
<220> FEATURE:
<223> OTHER INFORMATION: Synthetic antibacterial peptide derived from
      Bombina maxima

<400> SEQUENCE: 10

Gly Ile Gly Gly Val Leu Leu Ser Ala Gly Lys Ala Ala Leu Lys Gly
1               5                   10                  15

Leu Ala Lys Val Leu Ala Glu Lys Tyr Ala Asn
            20                  25

<210> SEQ ID NO 11
<211> LENGTH: 34
<212> TYPE: PRT
<213> ORGANISM: Artificial Sequence
<220> FEATURE:
<223> OTHER INFORMATION: Synthetic antibacterial peptide derived from
      Phyllomedusa sauvagii

<400> SEQUENCE: 11

Ala Leu Trp Lys Thr Met Leu Lys Lys Leu Gly Thr Met Ala Leu His
1               5                   10                  15

Ala Gly Lys Ala Ala Leu Gly Ala Ala Ala Asp Thr Ile Ser Gln Gly
            20                  25                  30

Thr Gln

<210> SEQ ID NO 12
<211> LENGTH: 26
<212> TYPE: PRT
<213> ORGANISM: Artificial Sequence
<220> FEATURE:
<223> OTHER INFORMATION: Synthetic antibacterial peptide derived from
      Litoria genimaculate

<400> SEQUENCE: 12

Gly Leu Leu Gln Thr Ile Lys Glu Lys Leu Glu Ser Leu Glu Ser Leu
1               5                   10                  15

Ala Lys Gly Ile Val Ser Gly Ile Gln Ala
            20                  25

<210> SEQ ID NO 13
<211> LENGTH: 17
<212> TYPE: PRT
<213> ORGANISM: Artificial Sequence
<220> FEATURE:
<223> OTHER INFORMATION: Synthetic antibacterial peptide, c-terminus
      amidated derived from Tityus serrulatus

<400> SEQUENCE: 13

Phe Leu Gly Met Ile Pro Gly Leu Ile Gly Gly Leu Ile Ser Ala Phe
1               5                   10                  15
```

Lys

<210> SEQ ID NO 14
<211> LENGTH: 26
<212> TYPE: PRT
<213> ORGANISM: Artificial Sequence
<220> FEATURE:
<223> OTHER INFORMATION: Synthetic antibacterial peptide, c-terminus
      amidated derived from Pleuronectes americanus

<400> SEQUENCE: 14

Gly Arg Arg Lys Arg Lys Trp Leu Arg Arg Ile Gly Lys Gly Val Lys
1               5                   10                  15

Ile Ile Gly Gly Ala Ala Leu Asp His Leu
            20                  25

<210> SEQ ID NO 15
<211> LENGTH: 19
<212> TYPE: PRT
<213> ORGANISM: Artificial Sequence
<220> FEATURE:
<223> OTHER INFORMATION: Synthetic antibacterial peptide derived from
      Ascaphus truei

<400> SEQUENCE: 15

Gly Phe Lys Asp Leu Leu Lys Gly Ala Ala Lys Ala Leu Val Lys Thr
1               5                   10                  15

Val Leu Phe

<210> SEQ ID NO 16
<211> LENGTH: 14
<212> TYPE: PRT
<213> ORGANISM: Artificial Sequence
<220> FEATURE:
<223> OTHER INFORMATION: Synthetic antibacterial peptide, c-terminus
      amidated derived from Polybia paulista

<400> SEQUENCE: 16

Ile Asp Trp Lys Lys Leu Leu Asp Ala Ala Lys Gln Ile Leu
1               5                   10

<210> SEQ ID NO 17
<211> LENGTH: 27
<212> TYPE: PRT
<213> ORGANISM: Artificial Sequence
<220> FEATURE:
<223> OTHER INFORMATION: Synthetic antibacterial peptide, c-terminus
      amidated

<400> SEQUENCE: 17

Lys Ile Leu Arg Gly Val Cys Lys Lys Ile Met Arg Thr Phe Leu Arg
1               5                   10                  15

Arg Ile Ser Lys Asp Ile Leu Thr Gly Lys Lys
            20                  25

<210> SEQ ID NO 18
<211> LENGTH: 21
<212> TYPE: PRT
<213> ORGANISM: Artificial Sequence
<220> FEATURE:
<223> OTHER INFORMATION: Synthetic antibacterial peptide, c-terminus
      amidated derived from Epinephelus coioides

<400> SEQUENCE: 18

Gly Phe Ile Phe His Ile Ile Lys Gly Leu Phe His Ala Gly Lys Met
1               5                   10                  15

Ile His Gly Leu Val
            20

<210> SEQ ID NO 19
<211> LENGTH: 18
<212> TYPE: PRT
<213> ORGANISM: Artificial Sequence
<220> FEATURE:
<223> OTHER INFORMATION: Synthetic antibacterial peptide, c-terminus
      amidated

<400> SEQUENCE: 19

Gly Ile Ile Lys Lys Ile Ile Lys Lys Ile Ile Lys Lys Ile Ile Lys
1               5                   10                  15

Lys Ile

<210> SEQ ID NO 20
<211> LENGTH: 33
<212> TYPE: PRT
<213> ORGANISM: Artificial Sequence
<220> FEATURE:
<223> OTHER INFORMATION: Synthetic antibacterial peptide derived from
      Pardachirus marmoratus

<400> SEQUENCE: 20

Gly Phe Phe Ala Leu Ile Pro Lys Ile Ile Ser Ser Pro Leu Phe Lys
1               5                   10                  15

Thr Leu Leu Ser Ala Val Gly Ser Ala Leu Ser Ser Ser Gly Gly Gln
            20                  25                  30

Glu

<210> SEQ ID NO 21
<211> LENGTH: 25
<212> TYPE: PRT
<213> ORGANISM: Artificial Sequence
<220> FEATURE:
<223> OTHER INFORMATION: Synthetic antibacterial peptide derived from
      Pleuronectes ferruginea

<400> SEQUENCE: 21

Arg Trp Gly Lys Trp Phe Lys Lys Ala Thr His Val Gly Lys His Val
1               5                   10                  15

Gly Lys Ala Ala Leu Thr Ala Tyr Leu
            20                  25

<210> SEQ ID NO 22
<211> LENGTH: 15
<212> TYPE: PRT
<213> ORGANISM: Artificial Sequence
<220> FEATURE:
<223> OTHER INFORMATION: Synthetic antibacterial peptide

<400> SEQUENCE: 22

Leu Lys Leu Leu Lys Lys Leu Leu Lys Lys Leu Leu Lys Leu Leu
1               5                   10                  15

<210> SEQ ID NO 23
<211> LENGTH: 23
<212> TYPE: PRT
<213> ORGANISM: Artificial Sequence
<220> FEATURE:
<223> OTHER INFORMATION: Synthetic antibacterial peptide derived from
      Xenopus laevis

<400> SEQUENCE: 23

```
Gly Ile Gly Lys Phe Leu His Ser Ala Gly Lys Phe Gly Lys Ala Phe
1               5                   10                  15

Val Gly Glu Ile Met Lys Ser
            20
```

<210> SEQ ID NO 24
<211> LENGTH: 21
<212> TYPE: PRT
<213> ORGANISM: Artificial Sequence
<220> FEATURE:
<223> OTHER INFORMATION: Synthetic antibacterial peptide derived from
      Bufo bufo gargarizans

<400> SEQUENCE: 24

```
Arg Ala Gly Leu Gln Phe Pro Val Gly Arg Leu Leu Arg Arg Leu Leu
1               5                   10                  15

Arg Arg Leu Leu Arg
            20
```

<210> SEQ ID NO 25
<211> LENGTH: 27
<212> TYPE: PRT
<213> ORGANISM: Artificial Sequence
<220> FEATURE:
<223> OTHER INFORMATION: Synthetic antibacterial peptide derived from
      Streptococcus pneumoniae

<400> SEQUENCE: 25

```
Met Arg Lys Glu Phe His Asn Val Leu Ser Ser Gly Gln Leu Leu Ala
1               5                   10                  15

Asp Lys Arg Pro Ala Arg Asp Tyr Asn Arg Lys
            20                  25
```

<210> SEQ ID NO 26
<211> LENGTH: 10
<212> TYPE: PRT
<213> ORGANISM: Artificial Sequence
<220> FEATURE:
<223> OTHER INFORMATION: Synthetic antibacterial peptide

<400> SEQUENCE: 26

```
Arg Arg Arg Arg Arg Asn Trp Met Trp Cys
1               5                   10
```

<210> SEQ ID NO 27
<211> LENGTH: 42
<212> TYPE: PRT
<213> ORGANISM: Artificial Sequence
<220> FEATURE:
<223> OTHER INFORMATION: Synthetic antibacterial peptide

<400> SEQUENCE: 27

```
Gly Ile Gly Lys Phe Leu His Ser Ala Lys Lys Phe Gly Lys Ala Phe
1               5                   10                  15

Val Gly Glu Ile Met Asn Ser Gly Gly Lys Lys Trp Lys Met Arg Arg
            20                  25                  30

Asn Gln Phe Trp Val Lys Val Gln Arg Gly
        35                  40
```

<210> SEQ ID NO 28
<211> LENGTH: 10
<212> TYPE: PRT
<213> ORGANISM: Artificial Sequence
<220> FEATURE:

```
<223> OTHER INFORMATION: Synthetic antibacterial peptide, c-terminus
      amidated

<400> SEQUENCE: 28

Gly Ile Ile Lys Lys Ile Ile Lys Lys Ile
1               5                   10

<210> SEQ ID NO 29
<211> LENGTH: 30
<212> TYPE: PRT
<213> ORGANISM: Artificial Sequence
<220> FEATURE:
<223> OTHER INFORMATION: Synthetic antibacterial peptide, containing
      three S-S bonds derived from Homo sapiens

<400> SEQUENCE: 29

Ala Cys Tyr Cys Arg Ile Pro Ala Cys Ile Ala Gly Glu Arg Arg Tyr
1               5                   10                  15

Gly Thr Cys Ile Tyr Gln Gly Arg Leu Trp Ala Phe Cys Cys
            20                  25                  30

<210> SEQ ID NO 30
<211> LENGTH: 35
<212> TYPE: PRT
<213> ORGANISM: Artificial Sequence
<220> FEATURE:
<223> OTHER INFORMATION: Synthetic antibacterial peptide, c-terminus
      amidated derived from Antheraea pernyi

<400> SEQUENCE: 30

Lys Trp Lys Val Phe Lys Lys Ile Glu Lys Met Gly Arg Asn Ile Arg
1               5                   10                  15

Asn Gly Ile Val Lys Ala Gly Pro Ala Ile Ala Val Leu Gly Glu Ala
            20                  25                  30

Lys Ala Leu
        35

<210> SEQ ID NO 31
<211> LENGTH: 24
<212> TYPE: PRT
<213> ORGANISM: Artificial Sequence
<220> FEATURE:
<223> OTHER INFORMATION: Synthetic antibacterial peptide derived from
      Homo sapiens

<400> SEQUENCE: 31

Asp Ser His Ala Lys Arg His His Gly Tyr Lys Arg Lys Phe His Glu
1               5                   10                  15

Lys His His Ser His Arg Gly Tyr
            20

<210> SEQ ID NO 32
<211> LENGTH: 13
<212> TYPE: PRT
<213> ORGANISM: Artificial Sequence
<220> FEATURE:
<223> OTHER INFORMATION: Synthetic antibacterial peptide, c-terminus
      amidated derived from Macropis fulvipes

<400> SEQUENCE: 32

Gly Phe Gly Met Ala Leu Lys Leu Leu Lys Lys Val Leu
1               5                   10

<210> SEQ ID NO 33
<211> LENGTH: 4
```

```
<212> TYPE: PRT
<213> ORGANISM: Artificial Sequence
<220> FEATURE:
<223> OTHER INFORMATION: Synthetic antibacterial peptide

<400> SEQUENCE: 33

Thr Lys Pro Arg
1

<210> SEQ ID NO 34
<211> LENGTH: 5
<212> TYPE: PRT
<213> ORGANISM: Artificial Sequence
<220> FEATURE:
<223> OTHER INFORMATION: Synthetic antibacterial peptide

<400> SEQUENCE: 34

His His Pro His Gly
1               5

<210> SEQ ID NO 35
<211> LENGTH: 10
<212> TYPE: PRT
<213> ORGANISM: Artificial Sequence
<220> FEATURE:
<223> OTHER INFORMATION: Synthetic antibacterial peptide

<400> SEQUENCE: 35

His His Pro His Gly His His Pro His Gly
1               5                   10

<210> SEQ ID NO 36
<211> LENGTH: 15
<212> TYPE: PRT
<213> ORGANISM: Artificial Sequence
<220> FEATURE:
<223> OTHER INFORMATION: Synthetic antibacterial peptide

<400> SEQUENCE: 36

His His Pro His Gly His His Pro His Gly His His Pro His Gly
1               5                   10                  15

<210> SEQ ID NO 37
<211> LENGTH: 20
<212> TYPE: PRT
<213> ORGANISM: Artificial Sequence
<220> FEATURE:
<223> OTHER INFORMATION: Synthetic antibacterial peptide

<400> SEQUENCE: 37

His His Pro His Gly His His Pro His Gly His His Pro His Gly His
1               5                   10                  15

His Pro His Gly
            20

<210> SEQ ID NO 38
<211> LENGTH: 4
<212> TYPE: PRT
<213> ORGANISM: Artificial Sequence
<220> FEATURE:
<223> OTHER INFORMATION: Synthetic antibacterial peptide, N-terminus
      acetylated and C-terminus amidated

<400> SEQUENCE: 38

Ala Ala Ala Lys
1
```

<210> SEQ ID NO 39
<211> LENGTH: 39
<212> TYPE: PRT
<213> ORGANISM: Artificial Sequence
<220> FEATURE:
<223> OTHER INFORMATION: Synthetic antibacterial peptide derived from
      Sus scrofa

<400> SEQUENCE: 39

Arg Arg Arg Pro Arg Pro Pro Tyr Leu Pro Arg Pro Arg Pro Pro
1               5                   10                  15

Phe Phe Pro Pro Arg Leu Pro Pro Arg Ile Pro Pro Gly Phe Pro Pro
                20                  25                  30

Arg Phe Pro Pro Arg Phe Pro
            35

<210> SEQ ID NO 40
<211> LENGTH: 7
<212> TYPE: PRT
<213> ORGANISM: Artificial Sequence
<220> FEATURE:
<223> OTHER INFORMATION: Synthetic antibacterial peptide, N-terminus
      acetylated and C-terminus amidated

<400> SEQUENCE: 40

Ala Ala Ala Ala Ala Ala Lys
1               5

<210> SEQ ID NO 41
<211> LENGTH: 13
<212> TYPE: PRT
<213> ORGANISM: Artificial Sequence
<220> FEATURE:
<223> OTHER INFORMATION: Synthetic antibacterial peptide

<400> SEQUENCE: 41

Phe Leu Gly Ala Leu Phe Lys Ala Leu Ser Lys Leu Leu
1               5                   10

<210> SEQ ID NO 42
<211> LENGTH: 20
<212> TYPE: PRT
<213> ORGANISM: Artificial Sequence
<220> FEATURE:
<223> OTHER INFORMATION: Synthetic antibacterial peptide, c-terminus
      amidated derived from Oreochromis mossambicus

<400> SEQUENCE: 42

Gln Ser His Leu Ser Leu Cys Arg Trp Cys Cys Asn Cys Cys Arg Ser
1               5                   10                  15

Asn Lys Gly Cys
            20

<210> SEQ ID NO 43
<211> LENGTH: 10
<212> TYPE: PRT
<213> ORGANISM: Artificial Sequence
<220> FEATURE:
<223> OTHER INFORMATION: Synthetic antibacterial peptide, N-terminus
      acetylated and C-terminus amidated

<400> SEQUENCE: 43

Ala Ala Ala Ala Ala Ala Ala Ala Ala Lys
1               5                   10

```
<210> SEQ ID NO 44
<211> LENGTH: 13
<212> TYPE: PRT
<213> ORGANISM: Artificial Sequence
<220> FEATURE:
<223> OTHER INFORMATION: Synthetic antibacterial peptide derived from
      Calliphora vicina

<400> SEQUENCE: 44

His Gly Val Ser Gly His Gly Gln His Gly Val His Gly
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic antibacterial peptide derived from
      Vigna sesquipedalis

<400> SEQUENCE: 45

Lys Thr Cys Glu Asn Leu Ala Asp Thr Tyr
1               5                   10

<210> SEQ ID NO 46
<211> LENGTH: 7
<212> TYPE: PRT
<213> ORGANISM: Artificial Sequence
<220> FEATURE:
<223> OTHER INFORMATION: Synthetic antibacterial peptide derived from
      Bacillus subtilis

<400> SEQUENCE: 46

Leu Leu Asp Val Leu Leu Glu
1               5

<210> SEQ ID NO 47
<211> LENGTH: 10
<212> TYPE: PRT
<213> ORGANISM: Artificial Sequence
<220> FEATURE:
<223> OTHER INFORMATION: Synthetic antibacterial peptide derived from
      Antennapedia

<400> SEQUENCE: 47

Glu Thr Phe Ser Asp Leu Trp Lys Leu Leu
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Synthetic antibacterial peptide

<400> SEQUENCE: 48

Ile Tyr Leu Gly Gly Pro Phe Ser Pro Asn Val Leu
1               5                   10

<210> SEQ ID NO 49
<211> LENGTH: 8
<212> TYPE: PRT
<213> ORGANISM: Artificial Sequence
<220> FEATURE:
<223> OTHER INFORMATION: Synthetic antibacterial peptide

<400> SEQUENCE: 49

Phe Glu Gln Asn Thr Ala Gln Pro
```

```
<210> SEQ ID NO 50
<211> LENGTH: 5
<212> TYPE: PRT
<213> ORGANISM: Artificial Sequence
<220> FEATURE:
<223> OTHER INFORMATION: Synthetic antibacterial peptide derived from
      Eisenia fetida

<400> SEQUENCE: 50

Ala Met Val Gly Thr
1               5

<210> SEQ ID NO 51
<211> LENGTH: 12
<212> TYPE: PRT
<213> ORGANISM: Artificial Sequence
<220> FEATURE:
<223> OTHER INFORMATION: Synthetic antibacterial peptide derived from
      Shell mollusk

<400> SEQUENCE: 51

Arg Asp Gly Asp Ser Cys Arg Gly Gly Gly Pro Val
1               5                   10

<210> SEQ ID NO 52
<211> LENGTH: 48
<212> TYPE: PRT
<213> ORGANISM: Artificial Sequence
<220> FEATURE:
<223> OTHER INFORMATION: Synthetic antibacterial peptide derived from
      Homo sapiens

<400> SEQUENCE: 52

Ser Ser Leu Leu Glu Lys Gly Leu Asp Gly Ala Lys Lys Ala Val Gly
1               5                   10                  15

Gly Leu Gly Lys Leu Gly Lys Asp Ala Val Glu Asp Leu Glu Ser Val
            20                  25                  30

Gly Lys Gly Ala Val His Asp Val Lys Asp Val Leu Asp Ser Val Leu
        35                  40                  45

<210> SEQ ID NO 53
<211> LENGTH: 20
<212> TYPE: PRT
<213> ORGANISM: Artificial Sequence
<220> FEATURE:
<223> OTHER INFORMATION: Synthetic antibacterial peptide derived from
      Homo sapiens

<400> SEQUENCE: 53

Ile Cys Ile Phe Cys Cys Gly Cys Cys His Arg Ser Lys Cys Gly Met
1               5                   10                  15

Cys Cys Lys Thr
            20
```